(12) United States Patent
Semler et al.

(10) Patent No.: US 8,906,110 B2
(45) Date of Patent: Dec. 9, 2014

(54) TWO PIECE CANCELLOUS CONSTRUCT FOR CARTILAGE REPAIR

(75) Inventors: Eric J. Semler, Piscataway, NJ (US); Katherine G. Truncale, Hillsborough, NJ (US); Alex B. Callahan, Perth Amboy, NJ (US); Judith I. Yannariello-Brown, Somerset, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 0 days.

(21) Appl. No.: 12/881,988

(22) Filed: Sep. 14, 2010

(65) Prior Publication Data

US 2011/0224797 A1 Sep. 15, 2011

Related U.S. Application Data

(63) Continuation of application No. 11/657,042, filed on Jan. 24, 2007, now Pat. No. 7,837,740.

(51) Int. Cl.
| | | |
|---|---|---|
| *A61F 2/28* | (2006.01) | |
| *A61L 27/36* | (2006.01) | |
| *A61L 27/38* | (2006.01) | |
| *A61L 27/54* | (2006.01) | |
| *A61F 2/30* | (2006.01) | |
| *A61F 2/46* | (2006.01) | |
| *A61B 17/00* | (2006.01) | |
| *A61F 2/38* | (2006.01) | |

(52) U.S. Cl.
CPC ... *A61F 2/30756* (2013.01); *A61F 2002/30225* (2013.01); *A61F 2002/30354* (2013.01);
(Continued)

(58) Field of Classification Search
USPC ...................................................... 623/23.63
See application file for complete search history.

(56) References Cited

U.S. PATENT DOCUMENTS

| | | |
|---|---|---|
| 3,400,199 A | 9/1968 | Balassa |
| 3,476,855 A | 11/1969 | Balassa |

(Continued)

FOREIGN PATENT DOCUMENTS

| | | |
|---|---|---|
| EP | 0517030 A2 | 12/1992 |
| EP | 0522569 A1 | 1/1993 |

(Continued)

OTHER PUBLICATIONS

U.S. Appl. No. 13/025,722, filed Feb. 11, 2011.

(Continued)

*Primary Examiner* — Thomas J Sweet
*Assistant Examiner* — Melissa Hoban
(74) *Attorney, Agent, or Firm* — Greenberg Traurig, LLP (57) ABSTRACT

The invention is directed toward a cartilage repair assembly comprising a shaped allograft two piece construct with a demineralized cancellous cap and a mineralized cylindrical base member defining a blind bore with a through-going transverse bore intersecting the blind bore. The demineralized cancellous cap has a cylindrical top portion and a smaller diameter cylindrical stem extending away from the top portion which fits into the blind bore of the mineralized base member. The cap stem defines a transverse through-going bore which is aligned with the through-going bore of the base member to receive a cylindrical cortical pin holding the cap within the base member. The shaped structure is dimensioned to fit in a drilled bore in a cartilage defect area so that the assembly engages the side wall of the drilled bore in an interference fit.

6 Claims, 4 Drawing Sheets

(52) U.S. Cl.
CPC .................. *A61F 2002/30604* (2013.01); *A61F 2002/30764* (2013.01); *A61F 2002/30057* (2013.01); *A61L 27/3608* (2013.01); *A61F 2002/30932* (2013.01); *A61L 27/3654* (2013.01); *A61L 2300/64* (2013.01); *A61F 2002/30789* (2013.01); *A61F 2002/30448* (2013.01); *A61F 2220/005* (2013.01); *A61F 2220/0025* (2013.01); *A61F 2002/30762* (2013.01); *A61L 27/38* (2013.01); *A61F 2002/30461* (2013.01); *A61F 2220/0033* (2013.01); *A61F 2002/30795* (2013.01); *A61F 2002/2842* (2013.01); *A61F 2/28* (2013.01); *A61F 2002/4635* (2013.01); *A61F 2002/30772* (2013.01); *A61F 2310/00365* (2013.01); *A61F 2220/0066* (2013.01); *A61F 2002/30459* (2013.01); *A61L 2430/06* (2013.01); *A61B 17/00491* (2013.01); *A61F 2/3859* (2013.01); *A61L 27/54* (2013.01); *A61F 2002/30759* (2013.01); *A61F 2002/4649* (2013.01); *A61F 2230/0069* (2013.01); *A61L 2300/414* (2013.01); *A61F 2002/30227* (2013.01); *A61F 2002/4646* (2013.01); *A61F 2002/30235* (2013.01); *A61F 2002/2817* (2013.01); *A61F 2002/30785* (2013.01); *A61F 2250/0039* (2013.01); *A61F 2220/0075* (2013.01); *A61F 2002/2839* (2013.01); *A61F 2002/30327* (2013.01); *A61F 2002/30233* (2013.01); *A61F 2002/30492* (2013.01); *A61F 2002/30059* (2013.01)
USPC ..................... 623/23.51; 623/23.72

(56) References Cited

U.S. PATENT DOCUMENTS

| | | |
|---|---|---|
| 3,478,145 A | 11/1969 | Balassa |
| 3,551,560 A | 12/1970 | Theile |
| 3,772,432 A | 11/1973 | Balassa |
| 3,867,728 A | 2/1975 | Stubstad et al. |
| 3,966,908 A | 6/1976 | Balassa |
| 4,060,081 A | 11/1977 | Yannas et al. |
| 4,172,128 A | 10/1979 | Theile et al. |
| 4,201,845 A | 5/1980 | Feder et al. |
| 4,296,100 A | 10/1981 | Franco |
| 4,378,347 A | 3/1983 | Franco |
| 4,394,370 A | 7/1983 | Jefferies |
| 4,400,833 A | 8/1983 | Kurland |
| 4,442,655 A | 4/1984 | Stroetmann |
| 4,458,678 A | 7/1984 | Yannas et al. |
| 4,479,271 A | 10/1984 | Bolesky et al. |
| 4,501,269 A | 2/1985 | Bagby |
| 4,505,266 A | 3/1985 | Yannas et al. |
| 4,600,574 A | 7/1986 | Lindner et al. |
| 4,609,551 A | 9/1986 | Caplan et al. |
| 4,627,853 A | 12/1986 | Campbell et al. |
| 4,642,120 A | 2/1987 | Nevo et al. |
| 4,656,137 A | 4/1987 | Balassa |
| 4,681,763 A | 7/1987 | Nathanson et al. |
| 4,683,195 A | 7/1987 | Mullis et al. |
| 4,683,202 A | 7/1987 | Mullis |
| 4,757,017 A | 7/1988 | Cheung |
| 4,776,173 A | 10/1988 | Kamarei et al. |
| 4,776,853 A | 10/1988 | Klement et al. |
| 4,795,467 A | 1/1989 | Piez et al. |
| 4,801,299 A | 1/1989 | Brendel et al. |
| 4,837,379 A | 6/1989 | Wienberg |
| 4,846,835 A | 7/1989 | Grande |
| 4,880,429 A | 11/1989 | Stone |
| 4,902,508 A | 2/1990 | Badylak et al. |
| 4,904,259 A | 2/1990 | Itay |
| 4,932,973 A | 6/1990 | Gendler |
| 4,950,296 A | 8/1990 | McIntyre |
| 4,950,483 A | 8/1990 | Ksander et al. |
| 4,955,911 A | 9/1990 | Frey et al. |
| 4,963,146 A | 10/1990 | Li |
| 4,963,489 A | 10/1990 | Naughton et al. |
| 4,965,188 A | 10/1990 | Mullis et al. |
| 4,971,954 A | 11/1990 | Brodsky et al. |
| 4,976,738 A | 12/1990 | Frey et al. |
| 4,978,355 A | 12/1990 | Frey et al. |
| 4,994,084 A | 2/1991 | Brennan |
| 4,994,559 A | 2/1991 | Moscatelli et al. |
| 5,002,071 A | 3/1991 | Harrell |
| 5,002,583 A | 3/1991 | Pitaru et al. |
| 5,007,934 A | 4/1991 | Stone |
| 5,032,508 A | 7/1991 | Naughton et al. |
| 5,041,138 A | 8/1991 | Vacanti et al. |
| 5,053,049 A | 10/1991 | Campbell |
| 5,053,050 A | 10/1991 | Itay |
| 5,067,963 A | 11/1991 | Khouri et al. |
| 5,067,964 A | 11/1991 | Richmond et al. |
| 5,073,373 A | 12/1991 | O'Leary et al. |
| 5,084,051 A | 1/1992 | Tormala et al. |
| 5,092,887 A | 3/1992 | Gendler |
| 5,118,512 A | 6/1992 | O'Leary et al. |
| 5,152,791 A | 10/1992 | Hakamatsuka et al. |
| 5,155,214 A | 10/1992 | Baird et al. |
| 5,191,067 A | 3/1993 | Lappi et al. |
| 5,195,892 A | 3/1993 | Gershberg |
| 5,206,023 A | 4/1993 | Hunziker |
| 5,226,914 A | 7/1993 | Caplan et al. |
| 5,236,456 A | 8/1993 | O'Leary et al. |
| 5,256,140 A | 10/1993 | Fallick |
| 5,260,420 A | 11/1993 | Burnouf-Radosevich et al. |
| 5,266,476 A | 11/1993 | Sussman et al. |
| 5,270,300 A | 12/1993 | Hunziker |
| 5,275,826 A | 1/1994 | Badylak et al. |
| 5,281,422 A | 1/1994 | Badylak et al. |
| 5,284,155 A | 2/1994 | Treadwell et al. |
| 5,290,558 A | 3/1994 | O'Leary et al. |
| 5,298,254 A | 3/1994 | Prewett et al. |
| 5,302,702 A | 4/1994 | Seddon et al. |
| 5,306,304 A | 4/1994 | Gendler |
| 5,306,311 A | 4/1994 | Stone et al. |
| 5,310,883 A | 5/1994 | Seddon et al. |
| 5,314,476 A | 5/1994 | Prewett et al. |
| 5,326,357 A | 7/1994 | Kandel |
| 5,329,846 A | 7/1994 | Bonutti |
| 5,336,616 A | 8/1994 | Livesey et al. |
| 5,338,772 A | 8/1994 | Bauer et al. |
| 5,352,463 A | 10/1994 | Badylak et al. |
| 5,354,557 A | 10/1994 | Oppermann et al. |
| 5,356,629 A | 10/1994 | Sander et al. |
| 5,368,858 A | 11/1994 | Hunziker |
| 5,372,821 A | 12/1994 | Badylak et al. |
| 5,380,328 A | 1/1995 | Morgan |
| 5,411,885 A | 5/1995 | Marx |
| 5,425,769 A | 6/1995 | Snyders, Jr. |
| 5,439,684 A | 8/1995 | Prewett et al. |
| 5,439,818 A | 8/1995 | Fiddes et al. |
| 5,443,950 A | 8/1995 | Naughton et al. |
| 5,445,833 A | 8/1995 | Badylak et al. |
| 5,464,439 A | 11/1995 | Gendler |
| 5,466,462 A | 11/1995 | Rosenthal et al. |
| 5,491,220 A | 2/1996 | Seddon et al. |
| 5,496,722 A | 3/1996 | Goodwin et al. |
| 5,507,813 A | 4/1996 | Dowd et al. |
| 5,510,396 A | 4/1996 | Prewett et al. |
| 5,512,460 A | 4/1996 | Nauro et al. |
| 5,513,662 A | 5/1996 | Morse et al. |
| 5,516,532 A | 5/1996 | Atala et al. |
| 5,516,533 A | 5/1996 | Badylak et al. |
| 5,545,222 A | 8/1996 | Bonutti |
| 5,549,904 A | 8/1996 | Juergensen et al. |
| 5,554,389 A | 9/1996 | Badylak et al. |
| 5,556,430 A | 9/1996 | Gendler |
| 5,569,272 A | 10/1996 | Reed et al. |
| 5,571,895 A | 11/1996 | Kurokawa et al. |
| 5,576,288 A | 11/1996 | Lappi et al. |
| 5,604,293 A | 2/1997 | Fiddes et al. |

(56) References Cited

U.S. PATENT DOCUMENTS

| | | |
|---|---|---|
| 5,607,474 A | 3/1997 | Athanasiou et al. |
| 5,614,496 A | 3/1997 | Dunstan et al. |
| 5,618,925 A | 4/1997 | Dupont et al. |
| 5,622,928 A | 4/1997 | Naruo et al. |
| 5,624,463 A | 4/1997 | Stone et al. |
| 5,631,011 A | 5/1997 | Wadstrom |
| 5,632,745 A | 5/1997 | Schwartz |
| 5,656,598 A | 8/1997 | Dunstan et al. |
| 5,662,710 A | 9/1997 | Bonutti |
| 5,679,637 A | 10/1997 | Lappi et al. |
| 5,681,353 A | 10/1997 | Li et al. |
| 5,695,998 A | 12/1997 | Badylak et al. |
| 5,700,476 A | 12/1997 | Rosenthal et al. |
| 5,700,774 A | 12/1997 | Hattersley et al. |
| 5,707,962 A | 1/1998 | Chen et al. |
| 5,713,374 A | 2/1998 | Pachence et al. |
| 5,716,413 A | 2/1998 | Walter et al. |
| 5,723,331 A | 3/1998 | Tubo et al. |
| 5,728,159 A | 3/1998 | Stroever et al. |
| 5,733,337 A | 3/1998 | Carr, Jr. et al. |
| 5,736,132 A | 4/1998 | Juergensen et al. |
| 5,736,372 A | 4/1998 | Vacanti et al. |
| 5,736,396 A | 4/1998 | Bruder et al. |
| 5,749,874 A | 5/1998 | Schwartz |
| 5,755,791 A | 5/1998 | Whitson et al. |
| 5,759,190 A | 6/1998 | Vibe-Hansen et al. |
| 5,769,899 A | 6/1998 | Schwartz et al. |
| 5,770,417 A | 6/1998 | Vacanti et al. |
| 5,782,835 A | 7/1998 | Hart et al. |
| 5,782,915 A | 7/1998 | Stone |
| 5,786,217 A | 7/1998 | Tubo et al. |
| 5,788,625 A | 8/1998 | Plouhar et al. |
| 5,800,537 A | 9/1998 | Bell |
| 5,814,084 A | 9/1998 | Grivas et al. |
| 5,842,477 A | 12/1998 | Naughton et al. |
| 5,846,931 A | 12/1998 | Hattersley et al. |
| 5,853,746 A | 12/1998 | Hunziker |
| 5,855,620 A | 1/1999 | Bishopric et al. |
| 5,859,208 A | 1/1999 | Fiddes et al. |
| 5,863,296 A | 1/1999 | Orton |
| 5,863,297 A | 1/1999 | Walter et al. |
| 5,866,415 A | 2/1999 | Villeneuve |
| 5,876,452 A | 3/1999 | Athanasiou et al. |
| 5,881,733 A | 3/1999 | Stone |
| 5,888,219 A | 3/1999 | Bonutti |
| 5,891,558 A | 4/1999 | Bell et al. |
| 5,893,888 A | 4/1999 | Bell |
| 5,899,936 A | 5/1999 | Goldstein |
| 5,899,939 A | 5/1999 | Boyce et al. |
| 5,904,716 A | 5/1999 | Gendler |
| 5,906,827 A | 5/1999 | Khouri et al. |
| 5,910,315 A | 6/1999 | Stevenson et al. |
| 5,916,265 A | 6/1999 | Hu |
| 5,922,028 A | 7/1999 | Plouhar et al. |
| 5,948,429 A | 9/1999 | Bell et al. |
| 5,955,438 A | 9/1999 | Pitaru et al. |
| 5,964,805 A | 10/1999 | Stone |
| 5,968,556 A | 10/1999 | Atala et al. |
| 5,972,368 A | 10/1999 | McKay |
| 5,972,385 A | 10/1999 | Liu et al. |
| 5,974,663 A | 11/1999 | Ikeda et al. |
| 5,989,269 A | 11/1999 | Vibe-Hansen et al. |
| 5,989,289 A | 11/1999 | Coates et al. |
| 5,989,866 A | 11/1999 | Deisher et al. |
| 5,998,170 A | 12/1999 | Arakawa et al. |
| 6,001,352 A | 12/1999 | Boyan et al. |
| 6,005,161 A | 12/1999 | Brekke et al. |
| 6,013,853 A | 1/2000 | Athanasiou et al. |
| 6,017,348 A | 1/2000 | Hart et al. |
| 6,025,334 A | 2/2000 | Dupont et al. |
| 6,025,538 A | 2/2000 | Yaccarino, III |
| 6,027,743 A | 2/2000 | Khouri et al. |
| 6,030,635 A | 2/2000 | Gertzman et al. |
| 6,037,171 A | 3/2000 | Larsson |
| 6,039,762 A | 3/2000 | McKay |
| 6,056,777 A | 5/2000 | McDowell |
| 6,060,640 A | 5/2000 | Pauley et al. |
| 6,074,663 A | 6/2000 | Delmotte et al. |
| 6,080,194 A | 6/2000 | Pachence et al. |
| 6,090,996 A | 7/2000 | Li |
| 6,090,998 A | 7/2000 | Grooms et al. |
| 6,096,081 A | 8/2000 | Grivas et al. |
| 6,096,347 A | 8/2000 | Geddes et al. |
| 6,110,209 A | 8/2000 | Stone |
| 6,110,482 A | 8/2000 | Khouri et al. |
| 6,123,731 A | 9/2000 | Boyce et al. |
| 6,132,472 A | 10/2000 | Bonutti |
| 6,143,293 A | 11/2000 | Weiss et al. |
| 6,146,385 A | 11/2000 | Torrie et al. |
| 6,156,068 A | 12/2000 | Walter et al. |
| 6,165,486 A | 12/2000 | Marra et al. |
| 6,165,487 A | 12/2000 | Ashkar et al. |
| 6,176,880 B1 | 1/2001 | Plouhar et al. |
| 6,180,605 B1 | 1/2001 | Chen et al. |
| 6,183,737 B1 | 2/2001 | Zaleske et al. |
| 6,189,537 B1 | 2/2001 | Wolfinbarger, Jr. |
| 6,197,061 B1 | 3/2001 | Masuda et al. |
| 6,197,586 B1 | 3/2001 | Bhatnagar et al. |
| 6,200,347 B1 | 3/2001 | Anderson et al. |
| 6,221,854 B1 | 4/2001 | Radomsky |
| 6,231,607 B1 | 5/2001 | Ben-Bassat et al. |
| 6,235,316 B1 | 5/2001 | Adkisson |
| 6,242,247 B1 | 6/2001 | Rieser et al. |
| 6,251,143 B1 | 6/2001 | Schwartz et al. |
| 6,258,778 B1 | 7/2001 | Rodgers et al. |
| 6,261,586 B1 | 7/2001 | McKay |
| 6,267,786 B1 | 7/2001 | Stone |
| 6,270,528 B1 | 8/2001 | McKay |
| 6,274,090 B1 | 8/2001 | Coelho et al. |
| 6,274,663 B1 | 8/2001 | Hosokawa et al. |
| 6,274,712 B1 | 8/2001 | Springer et al. |
| 6,280,473 B1 | 8/2001 | Lemperle et al. |
| 6,281,195 B1 | 8/2001 | Rueger et al. |
| 6,283,980 B1 | 9/2001 | Vibe-Hansen et al. |
| 6,288,043 B1 | 9/2001 | Spiro et al. |
| 6,293,970 B1 | 9/2001 | Wolfinbarger, Jr. |
| 6,294,187 B1 | 9/2001 | Boyce et al. |
| 6,294,359 B1 | 9/2001 | Fiddes et al. |
| 6,303,585 B1 | 10/2001 | Spiro et al. |
| 6,305,379 B1 | 10/2001 | Wolfinbarger, Jr. |
| 6,306,174 B1 | 10/2001 | Gei et al. |
| 6,306,177 B1 | 10/2001 | Felt et al. |
| 6,306,424 B1 | 10/2001 | Vyakarnam et al. |
| 6,310,267 B1 | 10/2001 | Rapp |
| 6,319,712 B1 | 11/2001 | Meenen et al. |
| 6,333,029 B1 | 12/2001 | Vyakarnam et al. |
| 6,352,558 B1 | 3/2002 | Spector |
| 6,352,971 B1 | 3/2002 | Diesher et al. |
| 6,361,565 B1 | 3/2002 | Bonutti |
| 6,365,405 B1 | 4/2002 | Salzmann et al. |
| 6,371,958 B1 | 4/2002 | Overaker |
| 6,376,244 B1 | 4/2002 | Atala |
| 6,379,367 B1 | 4/2002 | Vibe-Hansen et al. |
| 6,379,385 B1 | 4/2002 | Kalas et al. |
| 6,383,221 B1 | 5/2002 | Scarborough et al. |
| 6,387,693 B2 | 5/2002 | Rieser et al. |
| 6,398,811 B1 | 6/2002 | McKay |
| 6,398,816 B1 | 6/2002 | Brietbart et al. |
| 6,398,972 B1 | 6/2002 | Blasetti et al. |
| 6,432,436 B1 | 8/2002 | Gertzman et al. |
| 6,437,018 B1 | 8/2002 | Gertzman et al. |
| 6,440,141 B1 | 8/2002 | Philippon |
| 6,440,427 B1 | 8/2002 | Wadstrom |
| 6,440,444 B2 | 8/2002 | Boyce et al. |
| 6,451,060 B2 | 9/2002 | Masuda et al. |
| 6,454,811 B1 | 9/2002 | Sherwood et al. |
| 6,458,144 B1 | 10/2002 | Morris et al. |
| 6,458,158 B1 | 10/2002 | Anderson et al. |
| 6,458,375 B1 | 10/2002 | Gertzman et al. |
| 6,468,314 B2 | 10/2002 | Schwartz et al. |
| 6,471,993 B1 | 10/2002 | Shastri et al. |
| 6,475,175 B1 | 11/2002 | Rivera et al. |
| 6,486,377 B2 | 11/2002 | Rapp |
| 6,488,033 B1 | 12/2002 | Cerundolo |

(56) References Cited

U.S. PATENT DOCUMENTS

| | | | |
|---|---|---|---|
| 6,489,165 B2 | 12/2002 | Bhatnagar |
| 6,497,726 B1 | 12/2002 | Carter et al. |
| 6,503,277 B2 | 1/2003 | Bonutti |
| 6,504,079 B2 | 1/2003 | Tucker et al. |
| 6,511,511 B1 | 1/2003 | Slivka et al. |
| 6,511,958 B1 | 1/2003 | Atkinson et al. |
| 6,514,514 B1 | 2/2003 | Atkinson et al. |
| 6,520,964 B2 | 2/2003 | Tallarida et al. |
| 6,530,956 B1 | 3/2003 | Mansmann |
| 6,534,084 B1 | 3/2003 | Vyakarnam et al. |
| 6,541,024 B1 | 4/2003 | Kadiyala et al. |
| 6,548,729 B1 | 4/2003 | Seelich et al. |
| 6,569,172 B2 | 5/2003 | Asculai et al. |
| 6,576,015 B2 | 6/2003 | Geistlich et al. |
| 6,576,265 B1 | 6/2003 | Spievack |
| 6,579,538 B1 | 6/2003 | Spievack |
| 6,582,960 B1 | 6/2003 | Martin et al. |
| 6,591,581 B2 | 7/2003 | Schmieding |
| 6,592,598 B2 | 7/2003 | Vibe-Hansen et al. |
| 6,592,599 B2 | 7/2003 | Vibe-Hansen et al. |
| 6,599,300 B2 | 7/2003 | Vibe-Hansen et al. |
| 6,599,301 B2 | 7/2003 | Vibe-Hansen et al. |
| 6,599,515 B1 | 7/2003 | Delmotte |
| 6,623,963 B1 | 9/2003 | Muller et al. |
| 6,626,950 B2 | 9/2003 | Brown et al. |
| 6,630,000 B1 | 10/2003 | Bonutti |
| 6,632,247 B2 | 10/2003 | Boyer, II et al. |
| 6,652,592 B1 | 11/2003 | Grooms et al. |
| 6,652,593 B2 | 11/2003 | Boyer, II et al. |
| 6,652,872 B2 | 11/2003 | Nevo et al. |
| 6,662,805 B2 | 12/2003 | Frondoza et al. |
| 6,666,892 B2 | 12/2003 | Hiles et al. |
| 6,686,184 B1 | 2/2004 | Anderson et al. |
| 6,689,747 B2 | 2/2004 | Filvaroff et al. |
| 6,696,073 B2 | 2/2004 | Boyce et al. |
| 6,712,851 B1 | 3/2004 | Lemperle et al. |
| 6,727,224 B1 | 4/2004 | Zhang et al. |
| RE38,522 E | 5/2004 | Gertzman et al. |
| 6,730,314 B2 | 5/2004 | Jeschke et al. |
| 6,734,018 B2 | 5/2004 | Wolfinbarger, Jr. et al. |
| 6,743,232 B2 | 6/2004 | Overaker et al. |
| 6,752,834 B2 | 6/2004 | Geistlich et al. |
| 6,761,739 B2 | 7/2004 | Shepard |
| 6,761,887 B1 | 7/2004 | Kavalkovich et al. |
| 6,767,369 B2 | 7/2004 | Boyer et al. |
| 6,776,800 B2 | 8/2004 | Boyer, II et al. |
| 6,783,712 B2 | 8/2004 | Slivka et al. |
| 6,808,585 B2 | 10/2004 | Boyce et al. |
| 6,815,416 B2 | 11/2004 | Carney et al. |
| 6,838,440 B2 | 1/2005 | Stiles |
| 6,841,150 B2 | 1/2005 | Halvorsen et al. |
| 6,849,255 B2 | 2/2005 | Gazit et al. |
| 6,852,114 B2 | 2/2005 | Cerundolo |
| 6,852,125 B2 | 2/2005 | Simon et al. |
| 6,852,331 B2 | 2/2005 | Lai et al. |
| 6,855,167 B2 | 2/2005 | Shimp et al. |
| 6,855,169 B2 | 2/2005 | Boyer, II et al. |
| 6,858,042 B2 | 2/2005 | Nadler et al. |
| 6,866,668 B2 | 3/2005 | Giannetti et al. |
| 6,884,428 B2 | 4/2005 | Binette et al. |
| 6,890,354 B2 | 5/2005 | Steiner et al. |
| 6,893,462 B2 | 5/2005 | Buskirk et al. |
| 6,902,578 B1 | 6/2005 | Anderson et al. |
| 6,911,212 B2 | 6/2005 | Gertzman et al. |
| 6,932,977 B2 | 8/2005 | Heidaran et al. |
| 6,933,326 B1 | 8/2005 | Griffey et al. |
| 6,949,252 B2 | 9/2005 | Mizuno et al. |
| 6,989,034 B2 | 1/2006 | Hammer et al. |
| 6,993,328 B1 | 1/2006 | Oommen |
| 6,995,013 B2 | 2/2006 | Connelly et al. |
| 7,009,039 B2 | 3/2006 | Yayon et al. |
| 7,018,416 B2 | 3/2006 | Hanson et al. |
| 7,033,587 B2 | 4/2006 | Halvorsen et al. |
| 7,041,641 B2 | 5/2006 | Rueger et al. |
| 7,044,968 B1 | 5/2006 | Yaccarino, III et al. |
| 7,045,141 B2 | 5/2006 | Merboth et al. |
| 7,048,750 B2 | 5/2006 | Vibe-Hansen et al. |
| 7,048,762 B1 | 5/2006 | Sander et al. |
| 7,048,765 B1 | 5/2006 | Grooms et al. |
| 7,067,123 B2 | 6/2006 | Gomes et al. |
| 7,070,942 B2 | 7/2006 | Heidaran et al. |
| 7,078,232 B2 | 7/2006 | Konkle et al. |
| 7,087,082 B2 | 8/2006 | Paul et al. |
| 7,087,227 B2 | 8/2006 | Adkisson |
| 7,108,721 B2 | 9/2006 | Huckle et al. |
| RE39,321 E | 10/2006 | MacPhee et al. |
| 7,115,146 B2 | 10/2006 | Boyer, II et al. |
| 7,125,423 B2 | 10/2006 | Hazebrouck |
| 7,132,110 B2 | 11/2006 | Kay et al. |
| 7,137,989 B2 | 11/2006 | Asculai et al. |
| 7,141,072 B2 | 11/2006 | Geistlich et al. |
| 7,148,209 B2 | 12/2006 | Hoemann et al. |
| 7,156,880 B2 | 1/2007 | Evans et al. |
| 7,157,428 B2 | 1/2007 | Kusanagi et al. |
| 7,163,563 B2 | 1/2007 | Schwartz et al. |
| 7,166,133 B2 | 1/2007 | Evans et al. |
| 7,179,299 B2 | 2/2007 | Edwards et al. |
| 7,182,781 B1 | 2/2007 | Bianchi et al. |
| RE39,587 E | 4/2007 | Gertzman et al. |
| 7,201,917 B2 | 4/2007 | Malaviya et al. |
| 7,217,294 B2 | 5/2007 | Kusanagi et al. |
| 7,220,558 B2 | 5/2007 | Luyten et al. |
| 7,226,482 B2 | 6/2007 | Messerli et al. |
| 7,241,316 B2 | 7/2007 | Evans et al. |
| 7,252,987 B2 | 8/2007 | Bachalo et al. |
| 7,264,634 B2 | 9/2007 | Schmieding |
| 7,273,756 B2 | 9/2007 | Adkisson et al. |
| 7,288,406 B2 | 10/2007 | Bogin et al. |
| 7,291,169 B2 | 11/2007 | Hodorek |
| 7,297,161 B2 | 11/2007 | Fell |
| 7,316,822 B2 | 1/2008 | Binette et al. |
| 7,323,011 B2 | 1/2008 | Shepard et al. |
| 7,323,445 B2 | 1/2008 | Zhang et al. |
| 7,335,508 B2 | 2/2008 | Yayon et al. |
| 7,338,492 B2 | 3/2008 | Singhatat |
| 7,338,524 B2 | 3/2008 | Fell et al. |
| 7,358,284 B2 | 4/2008 | Griffey et al. |
| 7,361,195 B2 | 4/2008 | Schwartz et al. |
| 7,365,051 B2 | 4/2008 | Paulista et al. |
| 7,371,400 B2 | 5/2008 | Borenstein et al. |
| 7,416,889 B2 | 8/2008 | Ciombor et al. |
| 7,468,075 B2 | 12/2008 | Lang et al. |
| 7,468,192 B2 | 12/2008 | Mizuno et al. |
| 7,476,257 B2 | 1/2009 | Sah et al. |
| 7,479,160 B2 | 1/2009 | Branch et al. |
| 7,485,310 B2 | 2/2009 | Luyten et al. |
| 7,488,348 B2 | 2/2009 | Truncale et al. |
| 7,513,910 B2 | 4/2009 | Buskirk et al. |
| 7,531,000 B2 | 5/2009 | Hodorek |
| 7,537,617 B2 | 5/2009 | Bindsell et al. |
| 7,537,780 B2 | 5/2009 | Mizuno et al. |
| 7,548,865 B2 | 6/2009 | Schmieding |
| 7,550,007 B2 | 6/2009 | Malinin |
| 7,563,455 B2 | 7/2009 | McKay |
| 7,563,769 B2 | 7/2009 | Bogin et al. |
| 7,601,173 B2 | 10/2009 | Messerli et al. |
| 7,608,113 B2 | 10/2009 | Boyer, II et al. |
| 7,621,963 B2 | 11/2009 | Simon et al. |
| 7,622,438 B1 | 11/2009 | Lazarov et al. |
| 7,622,562 B2 | 11/2009 | Thorne et al. |
| 7,628,851 B2 | 12/2009 | Armitage et al. |
| 7,632,311 B2 | 12/2009 | Seedhom et al. |
| 7,638,486 B2 | 12/2009 | Lazarov et al. |
| 7,642,092 B2 | 1/2010 | Maor |
| 7,648,700 B2 | 1/2010 | Vignery et al. |
| 7,648,965 B2 | 1/2010 | Vignery et al. |
| 7,658,768 B2 | 2/2010 | Miller et al. |
| 7,662,184 B2 | 2/2010 | Edwards et al. |
| 7,666,230 B2 | 2/2010 | Orban et al. |
| RE41,286 E | 4/2010 | Atkinson et al. |
| 7,815,926 B2 | 10/2010 | Syring et al. |
| 7,824,701 B2 | 11/2010 | Binette et al. |
| 7,837,740 B2 | 11/2010 | Semler et al. |
| 7,875,296 B2 | 1/2011 | Binette et al. |

(56) References Cited

U.S. PATENT DOCUMENTS

| | | | |
|---|---|---|---|
| RE42,208 E | 3/2011 | Truncale et al. |
| 7,901,457 B2 | 3/2011 | Truncale et al. |
| 7,901,461 B2 | 3/2011 | Harmon et al. |
| 8,039,016 B2 | 10/2011 | Drapeau et al. |
| 8,137,702 B2 | 3/2012 | Binette et al. |
| 8,163,549 B2 | 4/2012 | Yao et al. |
| 8,258,117 B2 | 9/2012 | Hoemann |
| RE43,714 E | 10/2012 | Nadler |
| 8,282,953 B2 | 10/2012 | Drapeau |
| 8,318,212 B2 | 11/2012 | Malinin |
| 8,337,784 B2 | 12/2012 | Johnson |
| 8,343,218 B2 | 1/2013 | Lang |
| 8,419,802 B2 | 4/2013 | Evans |
| 8,431,147 B2 | 4/2013 | Drapeau |
| 8,480,757 B2 | 7/2013 | Gage |
| 8,496,970 B2 | 7/2013 | Binette et al. |
| 8,497,121 B2 | 7/2013 | Yao et al. |
| 8,518,433 B2 | 8/2013 | Kizer |
| 8,524,268 B2 | 9/2013 | Kizer |
| 8,556,972 B2 | 10/2013 | Gordon |
| 8,591,581 B2 | 11/2013 | Strzepa |
| 8,652,500 B2 | 2/2014 | Bosley, Jr. |
| 8,652,507 B2 | 2/2014 | Kizer |
| 2001/0005592 A1 | 6/2001 | Bhatnagar et al. |
| 2001/0006634 A1 | 7/2001 | Zaleske et al. |
| 2001/0010023 A1 | 7/2001 | Schwartz et al. |
| 2001/0011131 A1 | 8/2001 | Luyten et al. |
| 2001/0016646 A1 | 8/2001 | Rueger et al. |
| 2001/0018619 A1 | 8/2001 | Enzerink et al. |
| 2001/0020188 A1 | 9/2001 | Sander |
| 2001/0021875 A1 | 9/2001 | Enzerink et al. |
| 2001/0031254 A1 | 10/2001 | Bianchi et al. |
| 2001/0039457 A1 | 11/2001 | Boyer, II et al. |
| 2001/0039458 A1 | 11/2001 | Boyer, II et al. |
| 2001/0041941 A1 | 11/2001 | Boyer, II et al. |
| 2001/0043940 A1 | 11/2001 | Boyce et al. |
| 2001/0051834 A1 | 12/2001 | Frondoza et al. |
| 2002/0009805 A1 | 1/2002 | Nevo et al. |
| 2002/0016592 A1 | 2/2002 | Branch et al. |
| 2002/0035401 A1 | 3/2002 | Boyce et al. |
| 2002/0042373 A1 | 4/2002 | Carney et al. |
| 2002/0045940 A1 | 4/2002 | Giannetti et al. |
| 2002/0055783 A1 | 5/2002 | Tallarida et al. |
| 2002/0072806 A1 | 6/2002 | Buskirk et al. |
| 2002/0082704 A1 | 6/2002 | Cerundolo |
| 2002/0099448 A1 | 7/2002 | Hiles et al. |
| 2002/0106393 A1 | 8/2002 | Bianchi et al. |
| 2002/0111695 A1 | 8/2002 | Kandel |
| 2002/0120274 A1 | 8/2002 | Overaker et al. |
| 2002/0138143 A1 | 9/2002 | Grooms et al. |
| 2002/0177224 A1 | 11/2002 | Madry et al. |
| 2002/0192263 A1 | 12/2002 | Merboth et al. |
| 2003/0021827 A1 | 1/2003 | Malaviya et al. |
| 2003/0023316 A1 | 1/2003 | Brown et al. |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0039695 A1 | 2/2003 | Geistlich et al. |
| 2003/0040113 A1 | 2/2003 | Muzuno et al. |
| 2003/0044444 A1 | 3/2003 | Malaviya et al. |
| 2003/0049299 A1 | 3/2003 | Malaviya et al. |
| 2003/0050709 A1 | 3/2003 | Noth et al. |
| 2003/0055502 A1 | 3/2003 | Lang et al. |
| 2003/0077821 A1 | 4/2003 | Sah et al. |
| 2003/0078617 A1 | 4/2003 | Schwartz et al. |
| 2003/0099620 A1 | 5/2003 | Zaleske et al. |
| 2003/0100947 A1 | 5/2003 | Nadler |
| 2003/0139591 A1 | 7/2003 | Luyten et al. |
| 2003/0144743 A1 | 7/2003 | Edwards et al. |
| 2003/0229400 A1 | 12/2003 | Masuda et al. |
| 2003/0236573 A1 | 12/2003 | Evans et al. |
| 2004/0024457 A1 | 2/2004 | Boyce et al. |
| 2004/0028717 A1 | 2/2004 | Sittinger et al. |
| 2004/0033212 A1 | 2/2004 | Thomson et al. |
| 2004/0039447 A1 | 2/2004 | Simon et al. |
| 2004/0044408 A1 | 3/2004 | Hungerford et al. |
| 2004/0062753 A1 | 4/2004 | Rezania et al. |
| 2004/0078090 A1 | 4/2004 | Binette et al. |
| 2004/0102850 A1 | 5/2004 | Shepard |
| 2004/0107003 A1 | 6/2004 | Boyer, II et al. |
| 2004/0115172 A1 | 6/2004 | Bianchi et al. |
| 2004/0127987 A1* | 7/2004 | Evans et al. ............... 623/11.11 |
| 2004/0134502 A1 | 7/2004 | Mizuno et al. |
| 2004/0138748 A1 | 7/2004 | Boyer, II et al. |
| 2004/0143344 A1 | 7/2004 | Malaviya et al. |
| 2004/0151705 A1 | 8/2004 | Mizuno et al. |
| 2004/0166169 A1 | 8/2004 | Malaviya et al. |
| 2004/0170610 A1 | 9/2004 | Slavin et al. |
| 2004/0175826 A1 | 9/2004 | Maor |
| 2004/0192605 A1 | 9/2004 | Zhang et al. |
| 2004/0193268 A1 | 9/2004 | Hazebrouck |
| 2004/0197311 A1 | 10/2004 | Brekke et al. |
| 2004/0197373 A1 | 10/2004 | Gertzman et al. |
| 2004/0219182 A1 | 11/2004 | Gomes et al. |
| 2004/0220574 A1 | 11/2004 | Pelo et al. |
| 2004/0230303 A1 | 11/2004 | Gomes et al. |
| 2004/0241203 A1 | 12/2004 | Shakesheff et al. |
| 2004/0243242 A1 | 12/2004 | Sybert et al. |
| 2005/0004672 A1 | 1/2005 | Pafford et al. |
| 2005/0020500 A1 | 1/2005 | Shen et al. |
| 2005/0027307 A1 | 2/2005 | Schwartz et al. |
| 2005/0043814 A1 | 2/2005 | Kusanagi et al. |
| 2005/0064042 A1 | 3/2005 | Vunjak-Novakovic et al. |
| 2005/0065613 A1* | 3/2005 | Gross et al. ............... 623/23.51 |
| 2005/0074476 A1 | 4/2005 | Gendler et al. |
| 2005/0074481 A1 | 4/2005 | Brekke et al. |
| 2005/0089544 A1 | 4/2005 | Khouri et al. |
| 2005/0101957 A1 | 5/2005 | Buskirk et al. |
| 2005/0112761 A1 | 5/2005 | Halvorsen et al. |
| 2005/0125077 A1 | 6/2005 | Harmon et al. |
| 2005/0129668 A1 | 6/2005 | Giannetti et al. |
| 2005/0152882 A1 | 7/2005 | Kizer et al. |
| 2005/0159820 A1 | 7/2005 | Yoshikawa et al. |
| 2005/0159822 A1 | 7/2005 | Griffey et al. |
| 2005/0196460 A1 | 9/2005 | Malinin |
| 2005/0209705 A1 | 9/2005 | Niederauer et al. |
| 2005/0222687 A1 | 10/2005 | Vunjak-Novakovic et al. |
| 2005/0228498 A1 | 10/2005 | Andres |
| 2005/0240281 A1 | 10/2005 | Slivka et al. |
| 2005/0251268 A1 | 11/2005 | Truncale |
| 2005/0260612 A1 | 11/2005 | Padmini et al. |
| 2005/0261681 A9 | 11/2005 | Branch et al. |
| 2005/0261767 A1 | 11/2005 | Anderson et al. |
| 2005/0288796 A1 | 12/2005 | Awad et al. |
| 2006/0030948 A1 | 2/2006 | Manrique et al. |
| 2006/0060209 A1 | 3/2006 | Shepard |
| 2006/0099234 A1 | 5/2006 | Winkler |
| 2006/0111778 A1 | 5/2006 | Michalow |
| 2006/0167483 A1 | 7/2006 | Asculai et al. |
| 2006/0178748 A1 | 8/2006 | Dinger, III et al. |
| 2006/0200166 A1 | 9/2006 | Hanson et al. |
| 2006/0210643 A1 | 9/2006 | Truncale et al. |
| 2006/0216323 A1 | 9/2006 | Knaack et al. |
| 2006/0216822 A1 | 9/2006 | Mizuno et al. |
| 2006/0235534 A1 | 10/2006 | Gertzman et al. |
| 2006/0247790 A1 | 11/2006 | McKay |
| 2006/0247791 A1 | 11/2006 | McKay et al. |
| 2006/0251631 A1 | 11/2006 | Adkisson, IV et al. |
| 2006/0276907 A1 | 12/2006 | Boyer, II et al. |
| 2006/0293760 A1* | 12/2006 | McKay et al. ............... 623/23.5 |
| 2007/0009610 A1 | 1/2007 | Syring |
| 2007/0010824 A1 | 1/2007 | Malandain et al. |
| 2007/0014867 A1 | 1/2007 | Kusanagi et al. |
| 2007/0026030 A1 | 2/2007 | Gill et al. |
| 2007/0036834 A1 | 2/2007 | Pauletti et al. |
| 2007/0041950 A1 | 2/2007 | Leatherbury et al. |
| 2007/0055377 A1 | 3/2007 | Hanson et al. |
| 2007/0065943 A1 | 3/2007 | Smith et al. |
| 2007/0067032 A1 | 3/2007 | Felt et al. |
| 2007/0083266 A1 | 4/2007 | Lang |
| 2007/0093896 A1 | 4/2007 | Malinin |
| 2007/0093912 A1 | 4/2007 | Borden |

(56) References Cited

U.S. PATENT DOCUMENTS

| | | |
|---|---|---|
| 2007/0098759 A1 | 5/2007 | Malinin |
| 2007/0100450 A1 | 5/2007 | Hodorek |
| 2007/0113951 A1 | 5/2007 | Huang |
| 2007/0128155 A1 | 6/2007 | Sevedin |
| 2007/0134291 A1 | 6/2007 | Ting |
| 2007/0135917 A1 | 6/2007 | Malinin |
| 2007/0135918 A1 | 6/2007 | Malinin |
| 2007/0135928 A1 | 6/2007 | Malinin |
| 2007/0148242 A1 | 6/2007 | Vilei et al. |
| 2007/0162121 A1 | 7/2007 | Tarrant et al. |
| 2007/0168030 A1 | 7/2007 | Edwards et al. |
| 2007/0172506 A1 | 7/2007 | Nycz et al. |
| 2007/0178132 A1 | 8/2007 | Giannetti et al. |
| 2007/0179607 A1 | 8/2007 | Hodorek et al. |
| 2007/0185585 A1 | 8/2007 | Bracy et al. |
| 2007/0276506 A1 | 11/2007 | Troxel |
| 2007/0299517 A1 | 12/2007 | Davisson et al. |
| 2007/0299519 A1 | 12/2007 | Schmieding |
| 2008/0015709 A1 | 1/2008 | Evans et al. |
| 2008/0027546 A1 | 1/2008 | Semler et al. |
| 2008/0031915 A1 | 2/2008 | Becerra Ratia et al. |
| 2008/0038314 A1 | 2/2008 | Hunziker |
| 2008/0039939 A1 | 2/2008 | Iwamoto et al. |
| 2008/0039954 A1 | 2/2008 | Long et al. |
| 2008/0039955 A1 | 2/2008 | Hunziker |
| 2008/0051889 A1 | 2/2008 | Hodorek |
| 2008/0058953 A1 * | 3/2008 | Scarborough ............. 623/23.51 |
| 2008/0065210 A1 | 3/2008 | McKay |
| 2008/0077251 A1 | 3/2008 | Chen et al. |
| 2008/0086142 A1 | 4/2008 | Kohm et al. |
| 2008/0119947 A1 | 5/2008 | Huckle et al. |
| 2008/0125863 A1 | 5/2008 | McKay |
| 2008/0125868 A1 | 5/2008 | Branemark et al. |
| 2008/0133008 A1 | 6/2008 | Truncale et al. |
| 2008/0138414 A1 | 6/2008 | Huckle et al. |
| 2008/0153157 A1 | 6/2008 | Yao et al. |
| 2008/0154372 A1 | 6/2008 | Peckham |
| 2008/0167716 A1 | 7/2008 | Schwartz et al. |
| 2008/0183300 A1 | 7/2008 | Seedhom et al. |
| 2008/0220044 A1 | 9/2008 | Semler et al. |
| 2008/0249632 A1 * | 10/2008 | Stone et al. ................... 623/23.5 |
| 2008/0255676 A1 | 10/2008 | Semler et al. |
| 2008/0274157 A1 | 11/2008 | Vunjak-Novakovic et al. |
| 2008/0294270 A1 * | 11/2008 | Yao et al. .................... 623/23.63 |
| 2008/0305145 A1 | 12/2008 | Shelby et al. |
| 2009/0012629 A1 | 1/2009 | Yao et al. |
| 2009/0024223 A1 | 1/2009 | Chen et al. |
| 2009/0024224 A1 * | 1/2009 | Chen et al. ................. 623/23.72 |
| 2009/0036838 A1 | 2/2009 | Quelle et al. |
| 2009/0043389 A1 | 2/2009 | Vunjak-Novakovic et al. |
| 2009/0062870 A1 | 3/2009 | Milano et al. |
| 2009/0069901 A1 | 3/2009 | Truncale et al. |
| 2009/0069904 A1 | 3/2009 | Picha |
| 2009/0076624 A1 | 3/2009 | Rahaman et al. |
| 2009/0081276 A1 | 3/2009 | Alsberg et al. |
| 2009/0099661 A1 | 4/2009 | Bhattacharya et al. |
| 2009/0117652 A1 | 5/2009 | Luyten et al. |
| 2009/0131986 A1 | 5/2009 | Lee et al. |
| 2009/0149893 A1 | 6/2009 | Semler et al. |
| 2009/0210057 A1 | 8/2009 | Liao et al. |
| 2009/0226523 A1 | 9/2009 | Behnam et al. |
| 2009/0248592 A1 | 10/2009 | Schmieding |
| 2009/0253810 A1 | 10/2009 | Katz |
| 2009/0280179 A1 | 11/2009 | Neumann et al. |
| 2009/0291112 A1 | 11/2009 | Truncale et al. |
| 2009/0299475 A1 | 12/2009 | Yamamoto et al. |
| 2009/0312805 A1 | 12/2009 | Lang et al. |
| 2009/0312842 A1 | 12/2009 | Bursac et al. |
| 2009/0319045 A1 | 12/2009 | Truncale et al. |
| 2009/0319051 A9 | 12/2009 | Nycz et al. |
| 2009/0324722 A1 | 12/2009 | Elisseeff |
| 2010/0015202 A1 | 1/2010 | Semler et al. |
| 2010/0021521 A1 | 1/2010 | Xu et al. |
| 2010/0036492 A1 | 2/2010 | Hung et al. |
| 2010/0036503 A1 | 2/2010 | Chen et al. |
| 2010/0241228 A1 | 9/2010 | Syring et al. |
| 2010/0274362 A1 | 10/2010 | Yayon et al. |
| 2010/0305907 A1 | 12/2010 | Fitz |
| 2010/0322994 A1 | 12/2010 | Kizer et al. |
| 2011/0052705 A1 | 3/2011 | Malinin |
| 2011/0070271 A1 | 3/2011 | Truncale et al. |
| 2011/0104242 A1 | 5/2011 | Malinin |
| 2012/0009224 A1 | 1/2012 | Kizer et al. |
| 2012/0009230 A1 | 1/2012 | Drapeau et al. |
| 2012/0009270 A1 | 1/2012 | Kizer et al. |
| 2012/0107384 A1 | 5/2012 | Yao et al. |
| 2012/0156265 A1 | 6/2012 | Binette |
| 2012/0283833 A1 | 11/2012 | Brannon |
| 2013/0011442 A1 | 1/2013 | Chan |
| 2013/0071486 A1 | 3/2013 | McQuillan |
| 2013/0115255 A1 | 5/2013 | Bosley, Jr. |
| 2013/0123939 A1 | 5/2013 | Nauman |
| 2013/0158658 A1 | 6/2013 | Hayzlett |
| 2013/0158676 A1 | 6/2013 | Hayzlett |
| 2013/0197530 A1 | 8/2013 | McKay |
| 2013/0273121 A1 | 10/2013 | Mizuno |
| 2013/0287741 A1 | 10/2013 | Stilwell |
| 2013/0287753 A1 | 10/2013 | Centeno |
| 2013/0330391 A1 | 12/2013 | Malinin |
| 2013/0330415 A1 | 12/2013 | Yao et al. |
| 2013/0331898 A1 | 12/2013 | Nyemscek |
| 2014/0031795 A1 | 1/2014 | McKay |
| 2014/0065238 A1 | 3/2014 | Wolfinbarger, Jr. |

FOREIGN PATENT DOCUMENTS

| | | |
|---|---|---|
| EP | 0762903 A1 | 12/1995 |
| EP | 0517030 B1 | 9/1996 |
| EP | 0739631 A2 | 10/1996 |
| EP | 0784985 A1 | 7/1997 |
| EP | 0968012 A1 | 9/1998 |
| EP | 1099443 | 5/2001 |
| EP | 1237511 A1 | 6/2001 |
| EP | 1127581 A1 | 8/2001 |
| EP | 1181908 A1 | 2/2002 |
| EP | 1234552 A1 | 8/2002 |
| EP | 1234555 A2 | 8/2002 |
| EP | 0762903 B1 | 9/2003 |
| EP | 0739631 B1 | 12/2003 |
| EP | 1181908 B1 | 12/2003 |
| EP | 1384452 A1 | 1/2004 |
| EP | 1234555 A3 | 6/2004 |
| EP | 1237511 B1 | 9/2004 |
| EP | 1618178 A1 | 11/2004 |
| EP | 1127581 B1 | 6/2005 |
| EP | 1561481 A2 | 8/2005 |
| EP | 1234552 B1 | 8/2006 |
| EP | 0968012 B1 | 9/2006 |
| EP | 1719463 A1 | 11/2006 |
| EP | 1719531 A2 | 11/2006 |
| EP | 1719532 A2 | 11/2006 |
| EP | 1234555 B1 | 2/2007 |
| EP | 0762903 B2 | 8/2007 |
| EP | 1740121 A2 | 10/2007 |
| EP | 1537883 B1 | 4/2008 |
| EP | 1618178 B1 | 7/2008 |
| EP | 1416860 B1 | 3/2011 |
| GB | 2102811 A1 | 2/1983 |
| SU | 1454423 A1 | 1/1989 |
| WO | 84/04880 A1 | 12/1984 |
| WO | 93/16739 A1 | 9/1993 |
| WO | 94/03584 A1 | 2/1994 |
| WO | 95/25748 A1 | 9/1995 |
| WO | 95/33502 A1 | 12/1995 |
| WO | 96/24310 A1 | 8/1996 |
| WO | 97/37613 A1 | 10/1997 |
| WO | 98/14222 A1 | 4/1998 |
| WO | 98/34569 A1 | 8/1998 |
| WO | 98/41246 A2 | 9/1998 |
| WO | 98/43686 A1 | 10/1998 |
| WO | 90/01342 A1 | 2/1999 |
| WO | 99/08728 A1 | 2/1999 |
| WO | 99/09914 A1 | 3/1999 |
| WO | 99/11298 A2 | 3/1999 |

(56) References Cited

FOREIGN PATENT DOCUMENTS

| | | | |
|---|---|---|---|
| WO | 99/15209 A1 | 4/1999 |
| WO | 99/21497 A1 | 5/1999 |
| WO | 99/22747 A1 | 5/1999 |
| WO | 99/48541 A1 | 9/1999 |
| WO | 99/52572 A1 | 10/1999 |
| WO | 99/56797 A1 | 11/1999 |
| WO | 00/40177 A1 | 7/2000 |
| WO | 00/47114 A1 | 8/2000 |
| WO | 00/72782 A1 | 12/2000 |
| WO | 01/07595 A2 | 2/2001 |
| WO | 01/38357 A2 | 5/2001 |
| WO | 01/39788 A2 | 6/2001 |
| WO | 01/43667 A1 | 6/2001 |
| WO | 01/46416 A1 | 6/2001 |
| WO | 02/18546 A2 | 3/2002 |
| WO | 02/22779 A2 | 3/2002 |
| WO | 02/36732 A2 | 5/2002 |
| WO | 02/058484 A2 | 8/2002 |
| WO | 02/064180 A1 | 8/2002 |
| WO | 02/77199 A2 | 10/2002 |
| WO | 02/95019 A1 | 11/2002 |
| WO | 03/007805 A2 | 1/2003 |
| WO | 03/007873 A2 | 1/2003 |
| WO | 03/007879 A2 | 1/2003 |
| WO | 03/012053 A2 | 2/2003 |
| WO | 03/007879 A3 | 8/2003 |
| WO | 03/079985 A2 | 10/2003 |
| WO | 03/087160 A1 | 10/2003 |
| WO | 03/094835 A2 | 11/2003 |
| WO | 03/007805 A3 | 2/2004 |
| WO | 2004/067704 A2 | 8/2004 |
| WO | 2004/069298 A1 | 8/2004 |
| WO | 2004/075940 A1 | 9/2004 |
| WO | 2004/096983 A2 | 11/2004 |
| WO | 2004/103224 A1 | 12/2004 |
| WO | 2005058207 A1 | 6/2005 |
| WO | 2005/110278 A2 | 11/2005 |
| WO | 2004/096983 A3 | 12/2005 |
| WO | 2006/036681 A2 | 4/2006 |
| WO | 2006/042311 A2 | 4/2006 |
| WO | 2006/050213 A2 | 5/2006 |
| WO | 2005/110278 A3 | 8/2006 |
| WO | 02/036732 A3 | 9/2006 |
| WO | 2006/113586 A2 | 10/2006 |
| WO | 2006/042311 A3 | 11/2006 |
| WO | 03/094835 A3 | 3/2007 |
| WO | 2007/024238 A1 | 3/2007 |
| WO | 2006/113586 A3 | 7/2007 |
| WO | 2008/013763 A2 | 1/2008 |
| WO | 2008/021127 A2 | 2/2008 |
| WO | 2008/013763 A3 | 4/2008 |
| WO | 2008/038287 A2 | 4/2008 |
| WO | 2008/081463 A2 | 7/2008 |
| WO | 2008/106254 A2 | 9/2008 |
| WO | 2008/038287 A3 | 4/2009 |
| WO | 2009/076164 A2 | 6/2009 |
| WO | 2009/111069 A1 | 9/2009 |
| WO | 2009/155232 A1 | 12/2009 |
| WO | 2010/083051 A2 | 7/2010 |

OTHER PUBLICATIONS

U.S. Appl. No. 12/966,674, filed Dec. 13, 2010.
U.S. Appl. No. 12/931,427, filed Feb. 1, 2011.
Non-final Office Action with regard to U.S. Appl. No. 12/381,072, mailed Jan. 20, 2011.
Non-final Office Action with regard U.S. Appl. No. 12/924,132, mailed Mar. 1, 2011.
Guilak, Farshid; "Functional Tissue Engineering: The Role of Biomechanics in Articular Cartilage Repair", Clinical Orthopaedics and Related Research, No. 391 S, pp. S295-S305, (c) 2001 Lipponcott Williams & Wilkins, Inc., (11 pages).
Spangenberg, Kimberly, M. et al. "Histomorphometric Analysis of a Cell-Based Model of Cartilage Repair", Tissue Engineering, vol. 8, No. 5, 2002, (8 pages).
Non-Final Office Action mailed Apr. 15, 2010 in connection with U.S. Appl. No. 11/657,042.
International Preliminary Report on Patentability for PCT/US2009/001459, mailed on May 12, 2010.
Final Office Action mailed Mar. 22, 2010 in connection with U.S. Appl. No. 12/010,984.
Search Report and Written Opinion for International Patent Application No. PCT/US2004/010957, issued on Nov. 1, 2004.
International Preliminary Report on Patentability for International Patent Application No. PCT/US2004/010957, issued on Nov. 18, 2005.
Search Report and Written Opinion for International Patent Application No. PCT/US2005/030610, issued on Apr. 7, 2006.
International Preliminary Report on Patentability for International Patent Application No. PCT/US2005/030610, issued on Feb. 26, 2008.
Search Report and Written Opinion for International Patent Application No. PCT/US2005/036878, issued on Sep. 21, 2006.
International Preliminary Report on Patentability for International Patent Application No. PCT/US2005/036878, issued on Apr. 17, 2007.
Search Report and Written Opinion for International Patent Application No. PCT/US2005/008798, issued on Jun. 19, 2006.
International Preliminary Report on Patentability for International Patent Application No. PCT/US2005/008798, issued on Nov. 1, 2006.
Search Report and Written Opinion for International Patent Application No. PCT/US2004/010956, issued on Oct. 28, 2005.
International Preliminary Report on Patentability for International Patent Application No. PCT/US2004/010956, issued on Nov. 18, 2005.
Search Report and Written Opinion for International Patent Application No. PCT/US2005/051796, issued on Jun. 23, 2009.
International Preliminary Report on Patentability for International Patent Application No. PCT/US2008/051796, issued on Jul. 28, 2009.
Search Report and Written Opinion for International Patent Application No. PCT/US2008/085522, issued on Jul. 6, 2009.
Search Report and Written Opinion for International Patent Application No. PCT/US2009/001459, issued on Jul. 6, 2009.
Non-Final Office Action mailed Apr. 15, 2010 in connection with U.S. Appl. No. 12/079,629.
Non-Final Office Action mailed Apr. 12, 2010 in connection with U.S. Appl. No. 12/191,490.
Non-Final Office Action mailed Apr. 26, 2010 in connection with U.S. Appl. No. 12/147,042.
Matsuda et al. (1995) In Vivo Chondrogenesis in Collagen Sponge Sandwiched by Perichondrium. J. Biomater. Sci. Polymer Ed., vol. 7, No. 3, pp. 221-229.
Fujisato et al. (1996) Effect of basic fibroblast growth factor on cartilage regeneration in chondrocyte-seeded collagen sponge scaffold. Biomaterials, vol. 17, No. 2, pp. 155-162.
Non-final Office Action for U.S. Appl. No. 12/043,001, mailed May 11, 2011.
Supplemental Search Report for European Patent Application No. 05728956.3, dated May 2, 2011.
Non-final Office Action for U.S. Appl. No. 12/179,034, mailed Jun. 29, 2011.
Final Office Action for U.S. Appl. No. 12/381,072, mailed Jun. 27, 2011.
Non-final Office Action for U.S. Appl. No. 12/966,674, mailed Jul. 12, 2011.
Non-final Office Action for U.S. Appl. No. 12/924,132, mailed Jul. 18, 2011.
Cheng, et al., "Chondrogenic Deffentiation of Adipose-Derived Adult Stem Cells by a Porous Scaffold Derived from Native Articular Carilage Extracellular Matrix", Tissue Engineering: Part A, vol. 15, No. 2, (2009), pp. 231-241.
Lin et al., "The Chondrocyte: Biology and Clinical Application", Tissue Engineering, vol. 12, No. 7, (2006) pp. 1971-1984.
Umlauf et al., "Cartilage biology, pathology, and repair", Cell Mol. Life Sci. Vol. 67, (2010), pp. 4197-4211.

(56) References Cited

OTHER PUBLICATIONS

Communication pursuant to Article 94(3) EPC for European Patent Application No. 08 782.3. dated Aug. 9, 2011.
International Perliminary Report on Patentability for International Patent Application No. PCT/US2010/000108, mailed Jul. 28, 2011.
First Action Interview Pilot Program Pre-Interview Communication for U.S. Appl. No. 12/931,427, mailed Aug. 19, 2011.
Aston et al., "Repair of Articular Surfaces by Allografts of Articular and Growth-Plate Cartilage," Journal of Bone and Joint Surgery, Jan. 1986, vol. 68-B, No. 1; pp. 29-35.
Hoffman, "Hydrogels for Biomedical Applications", Advanced Drug Delivery Reviews, 2002, vol. 43, pp. 3-12.
Dahlberg et al., "Demineralized Allogeneic Bone Matrix for Cartilage Repair", Journal of Orthopaedic Research, 1991, vol. 9, pp. 11-19.
Lu et al., "Minced Cartilage without Cell Culture Serves as an Effective Intraoperative Cell Source for Cartilage Repair", Journal of Orthopaedic Research, Jun. 2006, vol. 24, pp. 1261-1270.
Stone et al., "Articular Cartilage Paste Grafting to Full-Thickness Articular Cartilage Knee Joint Lesions: A 2-to 12-Year Follow-up", Arthroscopy: The Journal of Arthoscopic and Related Surgery, Mar. 2006, vol. 22, No. 3, pp. 291-299.
Newman, "Articular Cartilage Repair", American Journal of Sports Medicine, 1998, vol. 26, No. 2, pp. 309-324.
Brittberg et al., "Treatment of Deep Cartilage Defects in the Knee with Autologous Chondrocyte Transplantation", New England Journal of Medicine, Oct. 6, 1994, vol. 331, No. 14, pp. 889-895.
Nixon et al., "Enhanced Repair of Extensive Articular Defects by Insulin-like Growth Factor-I-Laden Fibrin Composites", Journal of Orthopaedic Research, 1999; 17:475-487.
International Cartilage Repair Society, "Cartilage Injury Evaluation Package", www.cartilage.org, 2000.
Richardson et al., "Repair of Human Articular Cartilage After Implantation of Autologous Chondrocytes", Journal of Bone and Joint Surgery [Br], 1999; 81-B:1064-1068.
Brittberg et al., "Autologous Chondrocytes Used for Articular Cartilage Repair: An Update", Clinical Orthopaedics and Related Research, 2001; No. 391 Suppl: S337-S348.
Peterson et al., "Two-to 9-year Outcome After Autologous Chondrocyte Transplantation of the Knee", Clinical Orthopaedics and Related Research, 2000; No. 374: 212-234.
Peterson et al., "Autologous Chondrocyte Transplantation: Biomechanics and Long-term Durability", American Journal of Sports Medicine, 2002, vol. 30, No. 1, pp. 2-12.
Messner et al., "Cartilage Repair: A Critical Review", Acta Orthopaedica Scandinavica, 1996, vol. 67, No. 5, pp. 523-529.
Messner et al., "The Long-term Prognosis for Severe Damage to Weight-bearing Cartilage in the Knee: A 14-year Clinical and Radiographic Follow-up in 28 Young Athletes", Acta Orthopaedica Scandinavica, 1996, vol. 67, No. 2, pp. 165-168.
Buckwalter et al., "Articular Cartilage: Degeneration and Osteoarthritis, Repair, Regeneration, and Transplantation", AAOS Instructional Course Lectures, 1998; 47:487-504.
Breinan et al., "Effect of Cultured Autologous Chondrocytes on Repair of Chondral Defects in a Canine Model", Journal of Bone and Joint Surgery [Am], Oct. 1997; vol. 79-A, No. 10, 1439-1451.
Breinan et al., "Autologous Chondrocyte Implantation in a Canine Model: Change in Composition of Reparative Tissue with Time", Journal of Orthopaedic Research, 2001; 19:482-492.
Brittberg et al., "Rabbit Articular Cartilage Defects Treated with Autologous Cultured Chondrocytes", Clinical Orthopaedics and Related Research, 1996; 326:270-283.
Nehrer et al., "Chondrocyte-seeded Collagen Matrices Implanted in a Chondral Defect in a Canine Model", Biomaterials, 1998; 19:2313-2328.
Vunjak-Novakovic et al., "Bioreactor Cultivation Conditions Modulate the Composition and Mechanical Properties of Tissue-Engineered Cartilage", Journal of Orthopaedic Research, 1999; 17:130-138.

Bursac, "Collagen Network Contributions to Structure-Function Relationships in Cartilaginous Tissues in Compression" (Dissertation), Boston University College of Engineering, 2002.
Gooch et al., "IGF-I and Mechanical Environment Interact to Modulate Engineered Cartilage Development", Biochemical and Biophysical Research Communications, 2001; 286:909-915.
Pei et al., "Growth Factors for Sequential Cellular De-and Re-differentiation in Tissue Engineering", Biochemical and Biophysical Research Communications, 2002; 294:149-154.
Obradovic et al., "Integration of Engineered Cartilage", Journal of Orthopaedic Research, 19:1089-1097, 2001.
Schaefer et al., "Tissue Engineered Composites for the Repair of Large Osteochondral Defects", Arthritis & Rheumatism, 46(9): 2524-2534 (2002).
Pei et al., "Bioreactors Mediate the Effectiveness of Tissue Engineering Scaffolds", The FASEB Journal, 16:1691-1694, published online (Aug. 7, 2002), 10.1096/fj.02-0083fje.
Madry et al., "Gene Transfer of a Human Insulin-like Growth Factor I cDNA Enhances Tissue Engineering of Cartilage", Human Gene Therapy, 13: 1621-1630 (Sep. 1, 2002).
Pearson et al. (eds.), American Association of Tissue Banks, Standards for Tissue Banking, 2008 (12th ed.), pp. 53-56, 86-88.
Ornitz et al., "Protein Family Review: Fibroblast Growth Factors", Genome Biology (2001) 2(3): reviews 3005. 1-3005.12, available at http://genomebiology.com/2001/2/3/reviews/3005.1.
Loeser et al., "Basic Fibroblast Growth Factor Inhibits the Anabolic Activity of Insulin-like Growth Factor 1 and Osteogenic Protein 1 in Adult Human Articular Chondrocytes", Arthritis & Rheumatism, vol. 52, No. 12 (Dec. 2005), pp. 3910-3917.
Kato et al., "Fibroblast Growth Factor is an Inhibitor of Chondrocyte Terminal Differentiation", Journal of Biological Chemistry, vol. 265, No. 10 (Apr. 5, 1990) pp. 5903-5909.
Andrés et al., "A Pro-Inflammatory Signature Mediates FGF2-induced Angiogenesis", Journal of Cellular and Molecular Medicine, (Jun. 28, 2008), available at http://www.ncbi.nlm.nih.gov/pubmed/18624773.
Burger et al., "Fibroblast growth factor receptor-1 is expressed by endothelial progenitor cells", Blood, vol. 100, No. 10 (Nov. 15, 2002) 3527-35.
Baird, "Fibroblast growth factors: activities and significance of non-neurotrophin neurotrophic growth factors", Current Opinions in Neurobiology, (1994) 4:78-86.
Mazué et al., "Preclinical and Clinical Studies with Recombinant Human Basic Fibroblast Growth Factor", Annals New York Academy of Sciences, (1991) 329-340.
Aviles et al., "Testing clinical therapeutic angiogenesis using basic fibroblast growth factor (FGF-2)", British Journal of Pharmacology (2003) 140: 637-646.
Nolan et al., "Living Bone Grafts", BMJ, vol. 304, Jun. 13, 1992, pp. 1520 and 1521.
Stone et al., "One-Step American Technique of Articular Cartilage Paste Grafting to Traumatic and Arthritic Defects in the Knee Joint (2-7 Years Follow-Up)", downloaded from http:web.archive.org/web/20041205005845/http://www.stoneclinic.com/onestep.thm; published Dec. 5, 2004.
Feczko et al., "Experimental Results of Donor Site Filling for Autologous Osteochondral Mosaicplasty", Arthroscopy: The Journal of Arthroscopic and Related Surgery, vol. 19, No. 7 (Sep. 2003), pp. 755-761.
Nettles et al., "In Situ Crosslinkable Hyaluronan For Articular Cartilage Repair", 50th Annual Meeting of the Orthopaedic Research Society, Paper No. 0202 (Mar. 2004).
Nettles et al., "Photocrosslinkable Hyaluronan as a Scaffold for Articular Cartilage Repair", Annals of Biomedical Engineering, vol. 32, No. 3, Mar. 2004, pp. 391-397.
Peretti et al., "Cell-Based Bonding of Articular Cartilage: An Extended Study", Journal of Biomedical Materials Research, 64A, 2003, pp. 517-524.
Bugbee, "Fresh Osteochondral Allografting", Operative Techniques in Sports Medicine, Apr. 2000, vol. 8, No. 2, pp. 158-162.

(56) References Cited

OTHER PUBLICATIONS

Verbruggen et al., "Repair Function in Organ Cultured Human Cartilage. Replacement of Enzymatically Removed Proteoglycans During Longterm Organ Culture", The Journal of Rheumatology, 12:4, (1985), pp. 665-674.
Peretti et al., "Cell-based Tissue-Engineered Allogeneic Implant for Cartilage Repair" Tissue Engineering, 2000, vol. 6. No. 5, pp. 567-576.
Jackson et al., "Cartilage Substitute: Overview of Basic Science & Treatment Options", Journal of American Academy of Orthopaedic Surgeons, vol. 9, Jan./Feb. 2001, pp. 37-52.
Glowacki, Julie, "Engineered Cartilage, Bone, Joints and Menisci-Potential for Temporomandibular Joint Reconstruction", Cells Tissues Organs, vol. 169, Issue 3, 2001, pp. 302-308.
Peretti et al., "A Biomedical Analysis of an Engineered Cell-Scaffold Implant for Cartilage Repair", Annals of Plastic Surgery, 2001, vol. 46, No. 5, pp. 533-537.
Peretti et al., "Biomechanical Analysis of a Chondrocyte-Based Repair Model of Articular Cartilage", Tissue Engineering, Aug. 1, 1999, vol. 5. No. 4, pp. 317-326.
Peretti et al., "In Vitro Bonding of Pre-seeded Chondrocyte", Sport Sciences for Health, May 1, 2007, vol. 2, No. 1, pp. 29-33.
Peretti et al., "Bonding of Cartilage Matrices with Cultured Chondrocytes: An Experiential Model", Journal of Orthopedic Research, Jan. 1998, vol. 16, No. 1, pp. 89-95.
Hunziker, "Articular Cartilage Repair: Basic Science and Clinical Progress. A Review of the Current Status and Prospects", Osteoarthritis and Cartilage 2001, vol. 10, No. 6, pp. 432-463.
Chen et al., "Repair of Articular Cartilage Defects: Part I. Basic Science of Cartilage Healing", The American Journal of Orthopedics, Jan. 1999, pp. 31-33.
Chen et al., "Repair of Articular Cartilage Defects: Part II. Treatment Options", The American Journal of Orthopedics, Feb. 1999, pp. 88-96.
Buckwalter, "Articular Cartilage Injuries", Clinical Orthopaedics and Related Research, 2002, No. 402, pp. 21-37.
Nixon et al., "New Horizons in Articular Cartilage Repair", Proceedings of the Annual Convention of the AAEP, 2001, vol. 47, pp. 217-226.
Tsumaki et al. "Role of CDMP-1 in Skeletal Morphogenesis: Promotion of Mesenchymal Cell Recruitment and Chondrocyte Differentiation", J. Cell Biol., Jan. 1999, vol. 144, No. 1, 161-173.
Trzeciak et al., "Evaluation of Cartilage Reconstruction by Means of Autologous Chondrocyte Versus Periosteal Graft Transplantation: An Animal Study", Transplantation Proceedings, vol. 38 (2006), pp. 305-311.
Brighton et al., "Articular Cartilage Preservation and Storage-I. Application of Tissue Culture Techniques to the Storage of Viable Articular Cartilage", Arthritis and Rheumatism, vol. 22, No. 10 (Oct. 1979), pp. 1093-1101.
Mahadev et al., "Autogenous Osteochondral Morselised Grafts for Full Thickness Osteochondral Defects in the Knee Joints of Pigs", Singapore Medical Journal, 2001, vol. 42(9), pp. 410-416.
Hunziker, "Articular Cartilage Structure in Humans and Experimental Animals", Articular Cartilage and Osteoarthritis, Raven Press, ed., 2001, pp. 183-199.
Girotto et al., "Tissue-specific gene expression in chondrocytes grown on three-dimensional hyaluronic acid scaffolds", Biomaterials, vol. 24 (2003), pp. 3265-3275.
Gertzman et al., "A pilot study evaluating sodium hyaluronate as a carrier for freeze-dried demineralized bone powder", Cell and Tissue Banking, vol. 2, 2001, pp. 87-94.
Diduch et al., "Joint Repair: Treatment Options for Articular Cartilage Injury" Orthopedic Technology Review (2002) 4:24-27.
Gilbert, et al., "Decellularization of Tissues and Organs", Biomaterials (2006) 27:3675-3683.
OsteoSponge product information, Bacterin International Inc., May 2005.
http://www.stoneclinic.com/articularcartilagepastegrafting (Copyright 2009).
http://www.technobusiness-solutions.com/article-lyophilization1.html (published Feb. 12, 2002).
Crescenzi et al., "Hyaluron Linear and Crosslinked Derivatives as Potential/Actual Biomaterials", in Hyaluronan (2002), vol. 1 (Chemical, Biochemical and Biological Aspects), J. F. Kennedy et al., Ed., pp. 261-268.
Michielen et al., "Novel Biomaterials Based on Cross-linked Hyaluronon: Structural Investigations", in Hyaluronan (2002), vol. 1 (Chemical, Biochemical and Biological Aspects), J. F. Kennedy et al., Ed., pp. 269-276.
U.S. Appl. No. 12/147,042, based on U.S. Patent No. 7,067,123, filed Jun. 26, 2008, entitled: "Novel Glue for Cartilage Repair".
Non-final Office Action mailed Aug. 19, 2009 in connection with U.S. Appl. No. 12/147,042.
Non-final Office Action mailed Apr. 19, 2007 in connection with U.S. Appl. No. 11/151,270.
Final Office Action mailed Oct. 9, 2007 in connection with U.S. Appl. No. 11/151,270.
Advisory Action mailed Dec. 27, 2007 in connection with U.S. Appl. No. 11/151,270.
Non-final Office Action mailed Jul. 9, 2008 in connection with U.S. Appl. No. 11/151,270.
Non-final Office Action mailed Nov. 5, 2004 in connection with U.S. Appl. No. 10/438,883.
Non-final Office Action mailed May 3, 2005 in connection with U.S. Appl. No. 10/438,883.
Final Office Action mailed Oct. 18, 2005 in connection with U.S. Appl. No. 10/438,883.
Non-final Office Action mailed Feb. 6, 2007 in connection with U.S. Appl. No. 10/438,883.
Communication mailed Oct. 9, 2007 in connection with U.S. Appl. No. 10/438,883.
Non-final Office Action mailed Nov. 12, 2008 in connection with U.S. Appl. No. 10/438,883.
Non-final Office Action mailed Feb. 7, 2008 in connection with U.S. Appl. No. 10/815,778.
Final Office Action mailed Nov. 13, 2008 in connection with U.S. Appl. No. 10/815,778.
Non-final Office Action mailed Jul. 2, 2009 in connection with U.S. Appl. No. 10/815,778.
Final Office Action mailed Mar. 15, 2010 in connection with U.S. Appl. No. 10/815,778.
Non-final Office Action mailed Feb. 20, 2007 in connection with U.S. Appl. No. 10/960,960.
Final Office Action mailed Sep. 28, 2007 in connection with U.S. Appl. No. 10/960,960.
Non-final Office Action mailed May 18, 2009 in connection with U.S. Appl. No. 11/657,042.
Final Office Action mailed Dec. 28, 2009 in connection with U.S. Appl. No. 11/657,042.
Non-final Office Action mailed Jan. 14, 2010 in connection with U.S. Appl. No. 11/081,103.
Non-final Office Action mailed Jul. 22, 2009 in connection with U.S. Appl. No. 12/010,984.
Non-final Office Action mailed Oct. 5, 2005 in connection with U.S. Appl. No. 10/424,765.
Non-final Office Action mailed Dec. 18, 2007 in connection with U.S. Appl. No. 11/081,103.
Final Office Action mailed Sep. 19, 2008 in connection with U.S. Appl. No. 11/081,103.
Non-final Office Action mailed Jun. 3, 2009 in connection with U.S. Appl. No. 11/081,103.
Abraham, Judith A. et al., (1986) Human Basic Fibroblast Growth Factor: Nucleotide Sequence and Genomic Organization. EMBO Journal 5(10):2523-2528.
Agrawal, Sudhir et al., (1991) Pharmacokinetics. Biodistribution, And Stability of Oligodeoxynucleotide Phosphorothioates In Mice. Proc Natl Acad Sci. USA 88(17):7595-7599.
Arakawa, Tsutomu et al., (1993) Production and Characterization of an Analog of Acidic Fibroblast Growth Factor With Enhanced Stability and Biological Activity. Protein Engineering 6(5):541-546.

(56) References Cited

OTHER PUBLICATIONS

Bailly, Karine et al., (2000) Uncoupling of cell proliferation and differentiation activities of basic fibroblast growth factor. FASEB Journal 14(2):333-343.
Bange, Johannes et al., (2002) Cancer progression and tumor cell motility are associated with the FGFR4 Arg388 allele. Cancer Research 62(3):840-846.
Bork, Peer (2000) Powers and pitfalls in sequence analysis: The 70% hurdle. Genome Res. 10(4):398-400.
Bork, Peer and Bairoch, Amnon (1996) Go hunting in sequence databases but watch out for the traps. Trends in Genetics 12(10):425-427.
Brenner, Steven E. (1999) Errors in genome annotation. Trends in Genetics 15(4):132-133.
Cappellen, David et al., (1999) Frequent activating mutations of FGFR3 In human bladder arid cervix carcinomas. Nature Genetics 23(1):18-20.
Chusho, Hideki et al., (2001) Dwarfism and early death in mice lacking C-type Natriuretic Peptide. Proc Natl Acad Sci. 98(7):4016-4021.
Coughlin, Shaun R. et al., (1988) Acidic and basic fibroblast growth factors stimulate tyrosine kinase activity in vivo. J Biol Chem. 263(2):988-993.
Dell'Accio, Francesco et al., (2001) Molecular markers predictive of the capacity of expanded human articular chondrocytes to form stable cartilage in vivo, Arthritis Rheum. 44(7):1608-19.
Doerks, Tobias et al., (1998) Protein annotation: detective work for function prediction. Trends Genet. 14(6):248-250.
Dvorakova, Dana et al., (2001) Changes in the expression of FGFR3 in patients with chronic myeloid leukaemia receiving transplants of allogeneic peripheral blood stem cells British Journal Haematology 13(3):832-835.
Eriksson, A. Elisabeth et al., (1991) Three-dimensional structure of human basic fibroblast growth factor. Proc. Natl. Acad. Sci. USA 88:3441-3445 (XP002936511).
Ezzat Shereen et al., (2002) Targeted expression of A Human pituitary tumor-derived isoform of FGF Receptor-4 Recapitulates Pituitary Tumorigenesis. Journal of Clinical Investigation 109(1):69-77.
Faham, Salem et al., (1998) Diversity does make a difference: fibroblast growth factor-Heparin interactions. Curr Opin Struct Biol 8(5):578-586.
Fingl, Edward and Woodbury, Dixon M. (1975) General Principles. In: The Pharmacological Basis of Therapeutics. Fifth edition. Goodman, Louis S. and Gilman, Alfred editors. 1:1-45.
Gargiulo, B. J. et al., (2002) Phenotypic modulation of human articular chondrocytes by bistratene A. Eur Cell Mater. 3:9-18.
Givol, David and Yayon, Avner (1992) Complexity of FGF receptors: genetic basis for structural diversity and functional specificity FASEB J. 6(15):3362-3369.
Hecht, H. J. et al., (2000) Structure of fibroblast growth factor 9 shows a symmetric dimmer with unique receptor-and heparin-binding interfaces. Acta Cryst. D57:378-384.
Johnson, Daniel E. and Williams, Lewis T. (1993) Structural and functional diversity in the FGF receptor multigene family. Adv Cancer Res. 60:1-41.
Kirikoshi, Hiroyuki et al., (2000) Molecular cloning and characterization of Human FGF-20 on chromosome 8p21.3-p22. Biochem Biophys Res Commun. 274(2):337-343.
Kuroda, S. et al., (1999) Anabolic effect of aminoterminally truncated Fibroblast Growth Factor 4 (FGF4) on bone. Bone 25(4):431-437.
Nakatake, Yuhki et al., (2001) Identification of a novel fibroblast growth factor. FGF-22, preferentially expressed in the inner root sheath of the hair follicle. Biochim Biophys Acta. 1517(3):460-463.
Ngo, J. Thomas et al., (1994) Computational complexity, protein structure prediction, and the Levithal Paradox. In: The Protein Folding Problem and Tertiary Structure Prediction. K. Merz Jr. and S. Le Grand, Editors. 433-506 see also table of contents.
Nishimura, Tetsuya et al., (2000) Identification Of a Novel FGF, FGF-21, Preferentially Expressed In The Liver. Biochim Biophys Acta 1492(1):203-206.
Okada-Ban, Mai et al., (2000) Fibroblast growth factor-2. International Journal of Biochemistry & Cell Biology 32 (3):263-267.
Olsen, Shaun K. (2003) Fibroblast growth factor (FGF) homologous factors share structural but not functional homology with FGFs. J Biol Chem. 278(36):34226-342236.
Ornitz, David M. et al., (1996) Receptor specificity of the fibroblast growth factor family. J Biol Chem. 271(25)1 5292-7.
Ornitz, David M. (2000) FGFs, heparan sulfate and FGFRs: Complex interactions essential for development. Bio Essays 22:108-112.
Pellegrini, Luca et al., (2000) Crystal structure of fibroblast growth factor receptor ectodomain bound to ligand and heparin. Nature 407(6807):1029-1034.
Pillai, Omathanu and Panchagnula, Ramesh (2001) Polymers in drug delivery. Curr Opin Chem Biol 5 (4):447-451.
Plotnikov, Alexander N. et al., (1999) Structural basis for FGF receptor dimerization and activation. Cell 98 (5):641-650.
Plotnikov, Alexander N. et al., (2000) Crystal structures of two FGF-FGFR complexes reveal the determinants of ligand-receptor specificity. Cell 101(4): 413-424.
Sahni, Malika et al., (1999) FGF signaling inhibits chondrocyte proliferation and regulates bone development through the STAT-1 pathway Genes Devel.13(11):1361-1366.
Schlessinger, Joseph et al., (2000) Crystal structure of a ternary FGF-FGFR-1 Heparin complex reveals a dual role for heparin in FGFR binding and dimerization. Mol Cell 6(3):743-750.
Schmal, H. et al., (2007) bFGF influences human articular chondrocyte differentiation. Cytotherapy 9(2):184-93.
Seno, Masaharu et al., (1990) Carboxyl-terminal structure of basic fibroblast growth factor significantly contributes to its affinity for Heparin. Eur J Biochem. 188:239-245.
Shao, Zhang-Qiang et al., (2006) Effects of intramyocardial administration of slow-release basic fibroblast growth factor on angiogenesis and ventricular remodeling in a rat infarct model. Circ. J. 70(4):471-477.
Skolnik, Jeffrey and Fetrow, Jacquelyn S. (2000) From genes to protein structure and function: novel applications of computational approaches in the genomic era. Trends BioTechnol. 18(1):34-39.
Sleeman, Matthew et al., (2001) Identification of a new fibroblast growth factor receptor, FGFR5. Gene 271 (2):171-182.
Smith, Temple and Zhang, Xiaolin (1997) The challenges of genome sequence annotation or The devil is in the details. Nat Biotechnol. 15(12):1222-1223.
Springer, Barry A. et al., (1994) Identification and Concerted Function of Two Receptors Binding Surfaces on Basic Fibroblast Growth Factor Required for Mitogenesis. The Journal of Biological Chemistry 269(43):26879-26884.
Stauber, Deborah J. et al., (2000) Structural interactions of fibroblast growth factor receptor with its ligands. Proc Natl Acad Sci USA 97(1):49-54.
Vajo, Zoltan et al., (2000) The Molecular and Genetic Basis of Fibroblast Growth Factor Receptor 3 Disorders: The Achondroplasia Family of Skeletal Dysplasias, Muenke Craniosynostosis, and Crouzon Syndrome with Acanthosis Nigricans. Endocrine Rev. 21(1):23-39.
Wells, James A. (1990) Additivity of mutational effects in proteins. Biochemistry 29(37):8509-8517.
Yamashita, Tetsuo et al., (2000) Identification of a novel fibroblast growth factor, Fgf-23, preferentially expressed in the ventrolateral thalamic nucleus of the brain. Biochemical and Biophysical Research Communications 277 (2):494-498.
Yayon, Avner et al., (1991) Cell surface, heparin-like molecules are required for binding of basic fibroblast growth factor to its high affinity receptor. Cell 64(4):841-848.
Yee, Cindy J. et al., (2000) Analysis of fibroblast growth factor receptor 3 S249C mutation in cervical carcinoma. Journal of the National Cancer Institute 92(22):1848-1849.
Zhang, Jiandong et al., (1991) Three-dimensional structure of human basic fibroblast growth factor, a structural homolog of interleukin 1 Beta. Proc Natl Acad Sci. USA 88(8):3446-3450.

(56) References Cited

OTHER PUBLICATIONS

Zhu, Hengyi et al., (1995) Glu-96 of basic fibroblast growth factor is essential for high affinity receptor binding. Journal of Biological Chemistry 270(37):21869-21874.

Zhu, Hengyi et al., (1997) Analysis of high-affinity binding determinants in the receptor binding epitope of basic fibroblast growth factor. Protein Engineering 10(4):417-421.

Carr, M. E. Jr. and Alving, B. M. (1995) Effect of fibrin structure on plasmin-mediated dissolution of plasma clots. Blood Coag. Fibrinol. 6(6):567-573.

Carr, Marcus E. (1988) Fibrin formed in plasma is composed of fibers more massive than those formed from purified fibrinogen. Thromb. Haemost. 59(3):535-539.

Cook, James L. et al., (2003) Biocompatibility of three-dimensional chondrocyte grafts in large tibial defects of rabbits. Am J Vet Res. 64(1):12-20.

Gao, Jizong et al. (2002) Repair of osteochondral defect with tissue-engineered two-phase composite material of injectable calcium phosphate and hyaluronan sponge, Tissue Engin. 13(5):827-837.

Gruber, Reinhard et al., (2002) Platelets stimulate proliferation of bone cells: involvement of platelet-derived growth factor, microparticles and membranes. Clin Oral Implants Res. 13(5):529-535.

Haisch, A. et al., (2000) Preparation of a pure autologous biodegradable fibrin matrix for tissue engineering. Med Biol Eng Comput. 38(6):686-689.

Itokazu, M. et al., (1997) The sustained release of antibiotic from freeze-dried fibrin-antibioticcompound and efficacies in a rat model of osteomyelitis. Infection 25(6):359-363.

Sims, C. Derek et al., (1998) Tissue engineered neocartilage using plasma derived polymer substrates and chondrocytes. Plastic & Recon. Surg. 101(6):1580-1585.

"Young's Modulus." Entry on http://en.wikipedia.org. accessed Oct. 27, 2005. 3 pages.

Bradford, Marion M. (1976) A Rapid and Sensitive Method for the Quantitation of Microgram Quantities of Protein Utilizing the Principle of Protein-Dye Binding. Analytical Biochemistry 72(1-2):248-254.

Atala et al. (1993) Injectable alginate seeded with chondrocytes as a potential treatment for vesicoureteral reflux. J. of Urology 150(2 Pt 2):745-7.

Temenoff et al., "Review: Tissue engineering for regeneration of articular cartilage", Biomaterials 21 (2000) pp. 431-440.

Hunziker, "Articular cartilage repair: are the intrinsic biological constraints undermining this process insuperable?", Osteoarthritis and Cartilage 7 (1999) pp. 15-28.

Final Office Action for U.S. Appl. No. 11/081,103, mailed Aug. 11, 2010.

Non-Final Office Action for U.S. Appl. No. 12/010,984, mailed Aug. 16, 2010.

U.S. Appl. No. 12/924,132, filed Sep. 21, 2010.

International Preliminary Report on Patentability for International Patent Application No. PCT/US2008/085522, issued Jun. 10, 2010.

Non-final Office Action for U.S. Appl. No. 12/322,996, mailed Apr. 4, 2011.

Final Office Action for U.S. Appl. No. 12/179,034, mailed Jan. 27, 2012.

Non-final Office Action for U.S. Appl. No. 12/381,072, mailed Jan. 23, 2012.

First Action Interview Pilot Program Pre-Interview Communication for U.S. Appl. No. 12/508,892, mailed Jan. 17, 2012.

Non-final Office Action for U.S. Appl. No. 12/924,132, mailed Feb. 21, 2012.

First Action Interview Pilot Program Pre-Interview Communication for U.S. Appl. No. 12/696,366, mailed Oct. 13, 2011.

Non-final Office Action for U.S. Appl. No. 11/081,103, mailed Nov. 28, 2011.

Non-final Office Action for U.S. Appl. No. 12/508,892, mailed Dec. 7, 2011.

Sedgwick at al., "Studies into the influence of carrageenan-induced inflammation on articular cartilage degradation using implantaton into air pouches", British Journal of Experimental Pathology, vol. 66, (1985), pp. 445-453.

Non-final Office Action for U.S. Appl. No. 13/025,722, mailed May 1, 2013.

van Beuningen et al., "Transforming growth factor-beta 1 stimulates articular chondrocyte proteoglycan synthesis and induces osteophyte formation in the murine knee joint", Laboratory Investigation; a Journal of Technical Methods and Pathology, vol. 71, No. 2, (1994), pp. 279-290.

Glansbeek et al., "Stimulation of articular cartilage repair in established arthritis by local administration of transforming growth factor-beta into murine knee joints", Laboratory Investigation; a Journal of Technical Methods and Pathology, vol. 78, No. 2, (1998), pp. 133-142.

Wan et al., "TGF-[beta]/BMP signaling in cartilage and bone cells", Current Opinion in Orthopedics, vol. 13, Issue 5, Oct. 2002, pp. 368-374.

Seyedin et al. "Cartilage-inducing factor-A. Apparent identity to transforming growth factor-beta", Journal of Biol. Chem. vol. 261, No. 13, May 5, 1986, pp. 5693-5695.

Final Office Action for U.S. Appl. No. 12/381,072, mailed Sep. 6, 2013.

Communication pursuant to Article 94(3) EPC for European Patent Application No. 09 717 359.5, dated Nov. 19, 2013.

Communication pursuant to Article 94(3) EPC for European Patent Application No. 05 728 956.3, dated Sep. 2, 2013.

Non-Final Office Action, mailed Jun. 17, 2014, for U.S. Appl. No. 12/381,072.

Non-final Office Action for U.S. Appl. No. 12/381,072, mailed Feb. 24, 2014.

* cited by examiner

TWO PIECE CANCELLOUS CONSTRUCT FOR CARTILAGE REPAIR

RELATED APPLICATION

This application is a continuation of U.S. patent application Ser. No. 11/657,042 filed Jan. 24, 2007 now U.S. Pat. No. 7,837,740, the entire disclosure of which is incorporated by reference herein in its entirety.

BACKGROUND OF THE INVENTION

1. Field of the Invention

The present invention is generally directed toward an allograft cartilage repair implant and is more specifically directed toward a two piece allograft cancellous bone implant having a demineralized cancellous bone cap member and a mineralized or partially demineralized cancellous bone base member, both pieces being held together with an allograft bone pin. The construct is shaped for an interference fit implantation in a shoulder, knee, hip, or ankle joint. The base member is provided with an axially positioned blind bore and a plurality of smaller diameter through-going bores which allow transport of cellular materials throughout the implant site to stimulate cartilage growth.

2. Description of the Prior Art

Articular cartilage injury and degeneration present medical problems to the general population which are constantly addressed by orthopedic surgeons. Every year in the United States, over 500,000 arthroplastic or joint repair procedures are performed. These include approximately 125,000 total hip and 150,000 total knee arthroplastics and over 41,000 open arthroscopic procedure to repair cartilaginous defects of the knee.

In the knee joint, the articular cartilage tissue forms a lining which faces the joint cavity on one side and is linked to the subehondral bone plate by a narrow layer of calcified cartilage tissue on the other. Articular cartilage (hyaline cartilage) consists primarily of extracellular matrix with a sparse population of chondrocytes distributed throughout the tissue. Articular cartilage is composed of chondrocytes, type II collagen fibril meshwork, proteoglycans and water. Active chondrocytes are unique in that they have a relatively low turnover rate and are sparsely distributed within the surrounding matrix. The collagens give the tissue its form and tensile strength and the interaction of proteoglycans with water give the tissue its stiffness to compression, resilience and durability. The hyaline cartilage provides a low friction bearing surface over the bony parts of the joint. If the lining becomes worn or damaged resulting in lesions, joint movement may be painful or severely restricted. Whereas damaged bone typically can regenerate successfully, hyaline cartilage regeneration is quite limited because of it's limited regenerative and reparative abilities.

Articular cartilage lesions generally do not heal, or heal only partially under certain biological conditions due to the lack of nerves, blood vessels and a lymphatic system. The limited reparative capabilities of hyaline cartilage usually results in the generation of repair tissue that lacks the structure and biomechanical properties of normal cartilage. Generally, the healing of the defect results in a fibrocartilaginous repair tissue that lacks the structure and biomedical properties of hyaline cartilage and degrades over the course of time. Articular cartilage lesions are frequently associated with disability and with symptoms such as joint pain, locking phenomena and reduced or disturbed function. These lesions are difficult to treat because of the distinctive structure and function of hyaline cartilage. Such lesions are believed to progress to severe forms of osteoarthritis. Osteoarthritis is the leading cause of disability and impairment in middle-aged and older individuals, entailing significant economic, social and psychological costs. Each year, osteoarthritis accounts for as many as 39 million physician visits and more than 500,000 hospitalizations. By the year 2020, arthritis is expected to affect almost 60 million persons in the United States and to limit the activity of 11.6 million persons.

There are many current therapeutic methods being used. None of these therapies has resulted in the successful regeneration of hyaline-like tissue that withstands normal joint loading and activity over prolonged periods. Currently, the techniques most widely utilized clinically for cartilage defects and degeneration are not articular cartilage substitution procedures, but rather lavage, arthroscopic debridement, and repair stimulation. The direct transplantation of cells or tissue into a defect and the replacement of the defect with biologic or synthetic substitutions presently accounts for only a small percentage of surgical interventions. The optimum surgical goal is to replace the defects with cartilage-like substitutes so as to provide pain relief, reduce effusions and inflammation, restore function, reduce disability and postpone or alleviate the need for prosthetic replacement.

Lavage and arthroscopic debridement involve irrigation of the joint with solutions of sodium chloride, Ringer or Ringer and lactate. The temporary pain relief is believed to result from removing degenerative cartilage debris, proteolytic enzymes and inflammatory mediators. These techniques provide temporary pain relief, but have little or no potential for further healing.

Repair stimulation is conducted by means of drilling, abrasion arthroplasty or microfracture. Penetration into the subchondral bone induces bleeding and fibrin clot formation which promotes initial repair, however, the tissue formed is fibrous in nature and not durable. Pain relief is temporary as the tissue exhibits degeneration, loss of resilience, stiffness and wear characteristics over time.

The periosteum and perichondrium have been shown to contain mesenchymal progenitor cells capable of differentiation and proliferation. They have been used as grafts in both animal and human models to repair articular defects. Few patients over 40 years of age obtain good clinical results, which most likely reflect the decreasing population of osteochondral progenitor cells with increasing age. There have also been problems with adhesion and stability of the grafts, which result in their displacement or loss from the repair site.

Transplantation of cells grown in culture provides another method of introducing a new cell population into chondral and osteochondral defects. CARTICELL® is a commercial process to culture a patient's own cartilage cells for use in the repair of cartilage defects in the femoral condyle marketed by Genzyme Biosurgery in the United States and Europe. The procedure uses arthroscopy to take a biopsy from a healthy, less loaded area of articular cartilage. Enzymatic digestion of the harvested tissue releases the cells that are sent to a laboratory where they are grown for a period ranging from 2-5 weeks. Once cultivated, the cells are injected during a more open and extensive knee procedure into areas of defective cartilage where it is hoped that they will facilitate the repair of damaged tissue. An autologous periosteal flap with a cambium layer is used to seal the transplanted cells in place and act as a mechanical barrier. Fibrin glue is used to seal the edges of the flap. This technique preserves the subchondral bone plate and has reported a high success rate. Proponents of this procedure report that it produces satisfactory results, including the ability to return to demanding physical activities, in more than 90% of patients and those biopsy specimens of the tissue in the graft sites show hyaline-like cartilage repair. More work is needed to assess the function and durability of the new tissue and determine whether it improves joint function and delays or prevents joint degeneration. As with the perichondrial graft, patient/donor age may compromise the success of this procedure as chondrocyte population decreases with increasing age. Disadvantages to this procedure include the need for two separate surgical procedures, potential damage to surrounding cartilage when the periosteal patch is sutured in place, the requirement of demanding microsurgical techniques, and the expensive cost of the procedure which is currently not covered by insurance.

Figure 1:
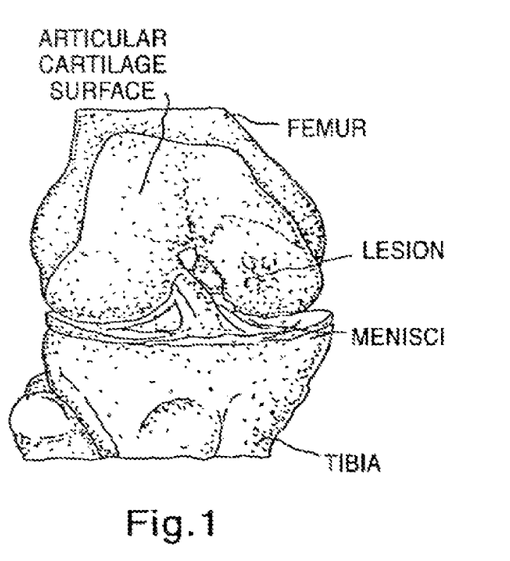
FIG. 1 is an anatomical illustration of a knee joint having articular cartilage in which a lesion has formed.
Figure 2:
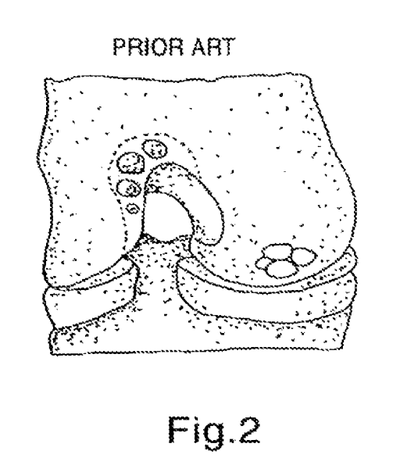
FIG. 2 is a schematic illustration of a mosaicplasty procedure, as known in the prior art.
Figure 3:
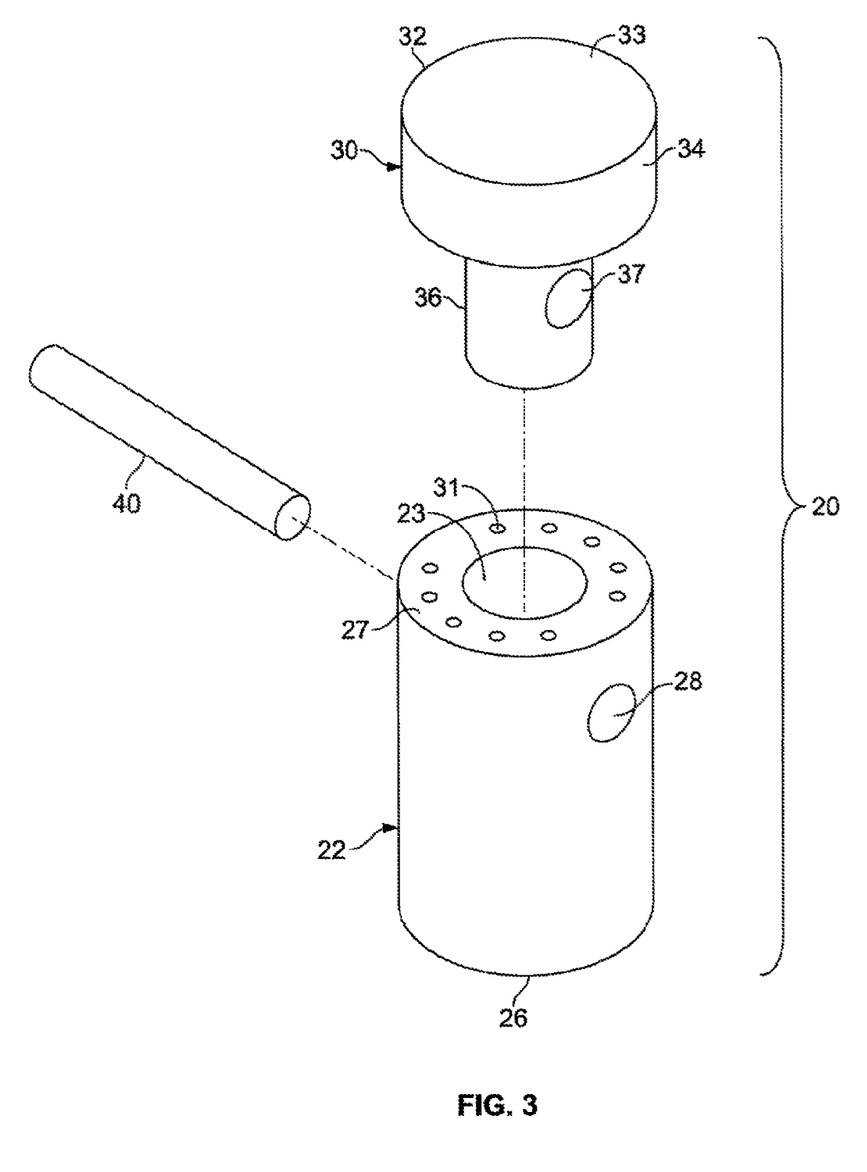
FIG. 3 is an exploded perspective view of a cancellous construct produced in accordance with an exemplary embodiment of the present invention.

Osteochondral transplantation or mosaicplasty involves excising all injured or unstable tissue from the articular defect and creating cylindrical holes in the base of the defect and underlying bone. These holes are filled with autologous cylindrical plugs of healthy cartilage and bone in a mosaic fashion. The osteochondral plugs are harvested from a lower weight-bearing area of lesser importance in the same joint. This technique, shown in Prior Art FIG. 2, can be performed as arthroscopic or open procedures. Reports of results of osteochondral plug autografts in a small numbers of patients indicate that they decrease pain and improve joint function, however, long-term results have not been reported. Factors that can compromise the results include donor site morbidity, effects of joint incongruity on the opposing surface of the donor site, damage to the chondrocytes at the articular margins of the donor and recipient sites during preparation and implantation, and collapse or settling of the graft over time. The limited availability of sites for harvest of osteochondral autografts restricts the use of this approach to treatment of relatively small articular defects and the healing of the chondral portion of the autograft to the adjacent articular cartilage remains a concern.

Transplantation of large allografts of bone and overlying articular cartilage is another treatment option that involves a greater area than is suitable for autologous cylindrical plugs, as well as for a non-contained defect. The advantages of osteochondral allografts are the potential to restore the anatomic contour of the joint, lack of morbidity related to graft harvesting, greater availability than autografts and the ability to prepare allografts in any size to reconstruct large defects. Clinical experience with fresh and frozen osteochondral allografts shows that these grafts can decrease joint pain, and that the osseous portion of an allograft can heal to the host bone and the chondral portion can function as an articular surface. Drawbacks associated with this methodology in the clinical situation include the scarcity of fresh donor material and problems connected with the handling and storage of frozen tissue. Fresh allografts carry the risk of immune response or disease transmission. Musculoskeletal Transplant Foundation (MTF) has preserved fresh allografts in a media that maintains a cell viability of 50% for 35 days for use as implants. Frozen allografts lack cell viability and have shown a decreased amount of proteoglycan content which contribute to deterioration of the tissue.

A number of United States patents have been specifically directed towards bone plugs which are implanted into a bone defect. Examples of such bone plugs are U.S. Pat. No. 4,950,296 issued Aug. 21, 1990 which discloses a bone graft device comprising a cortical shell having a selected outer shape and a cavity formed therein for receiving a cancellous plug, which is fitted into the cavity in a manner to expose at least one surface; U.S. Pat. No. 6,039,762 issued Mar. 21, 2000 discloses a cylindrical shell with an interior body of deactivated bone material and U.S. Pat. No. 6,398,811 issued Jun. 4, 2002 directed toward a bone spacer which has a cylindrical cortical bone plug with an internal through-going bore designed to hold a reinforcing member. U.S. Pat. No. 6,383,211 issued May 7, 2002 discloses an invertebral implant having a substantially cylindrical body with a through-going bore dimensioned to receive bone growth materials.

U.S. Pat. No. 6,379,385 issued Apr. 30, 2002 discloses an implant base body of spongious bone material into which a load carrying support element is embedded. The support element can take the shape of a diagonal cross or a plurality of cylindrical pins. See also, U.S. Pat. No. 6,294,187 issued Sep. 25, 2001 which is directed to a load bearing osteoimplant made of compressed bone particles in the form of a cylinder. The cylinder is provided with a plurality of through-going bores to promote blood flow through the osteoimplant or to hold a demineralized bone and glycerol paste mixture. U.S. Pat. No. 6,096,081 issued Aug. 1, 2000 shows a bone dowel with a cortical end cap or caps at both ends, a brittle cancellous body and a through-going bore.

While these implants have been used for bone tissue regeneration, the same will not work to repair cartilage areas due to the osteoinductive nature of the bone which causes bone growth.

The use of implants for cartilage defects is much more limited. Aside from the fresh allograft implants and autologous implants, U.S. Pat. No. 6,110,209 issued Nov. 5, 1998 shows the use an autologous articular cartilage cancellous bone paste to fill arthritic defects. The surgical technique is arthroscopic and includes debriding (shaving away loose or fragmented articular cartilage), followed by morselizing the base of the arthritic defect with an awl until bleeding occurs. An osteochondral graft is then harvested from the inner rim of the intercondylar notch using a trephine. The graft is then morselized in a bone graft crusher, mixing the articular cartilage with the cancellous bone. The paste is then pushed into the defect and secured by the adhesive properties of the bleeding bone. The paste can also be mixed with a cartilage stimulating factor, a plurality of cells, or a biological glue. All patients are kept non-weight bearing for four weeks and used a continuous passive motion machine for six hours each night. Histologic appearance of the biopsies has mainly shown a mixture of fibrocartilage with hyaline cartilage. Concerns associated with this method are harvest site morbidity and availability, similar to the mosaicplasty method.

U.S. Pat. No. 6,379,367 issued Apr. 30, 2002 discloses a plug with a base membrane, a control plug, and a top membrane which overlies the surface of the cartilage covering the defective area of the joint.

SUMMARY OF THE INVENTION

A cartilage repair allograft construct implant comprising a two piece allograft bone construct with a mineralized cylindrical cancellous bone base member and a demineralized and non-osteoinductive cancellous bone cap member that is mounted in a blind bore cut in the cancellous bone base member. The base and cap members are held together by an allograft bone pin. The two piece construct is used for replacing articular cartilage defects and is placed in a bore which has been cut into the patient to remove the lesion defect area. The bone base member has an axially aligned blind bore, at least one transverse lateral bore which intersects the blind bore, and has a plurality of longitudinal through-going bores which extend parallel to the axis of the cylindrical bone base member. The cap member has a stem which fits into the blind bore of the base member with the stem defining a transverse radial bore. The bottom surface of the cap member overlies the upper surface of the cylindrical base member with the radial bore of the stem and the longitudinal bore(s) of the base member being aligned to receive a cortical bone pin. Additives may be applied to the lateral and/or radial bores, the blind bore or the cap member of the construct in order to increase or accelerate cartilaginous or bony tissue formation. Each allograft construct can support the addition of a variety of chondrogenic stimulating factors including, but not limited to, morselized allogenic cartilage, growth factors (FGF-2, FGF-5, IGF-1, TGF-β, BMP-2, BMP-7, PDGF, VEGF), human allogenic or autologous chondrocytes, human allogenic or autologous bone marrow cells, stem cells, demineralized bone matrix, insulin, insulin-like growth factor-1, transforming growth factor-B, interleukin-1 receptor antagonist, hepatocyte growth factor, platelet-derived growth factor, Indian hedgehog and parathyroid hormone-related peptide or bioactive glue. It is also an object of the invention to provide a cartilage repair implant which is easily placed in a defect area by the surgeon using an arthroscopic, minimally invasive technique.

It is also an object of the invention to provide a cartilage repair implant which is easily placed in a defect area by the surgeon using an arthroscopic, minimally invasive technique.

It is still another object of the invention to provide an allograft implant which has load bearing capabilities.

It is further an object of the invention to provide an allograft implant procedure which is applicable for both partial and full thickness lesions.

It is yet another object of the invention to provide an allograft implant which facilitates growth of hyaline cartilage.

It is an additional object of the invention to provide a cancellous construct which is treated with chondrogenic stimulating factors.

These and other objects, advantages, and novel features of the present invention will become apparent when considered with the teachings contained in the detailed disclosure along with the accompanying drawings.

BRIEF DESCRIPTION OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention.

DESCRIPTION OF THE INVENTION

The term "tissue" is used in the general sense herein to mean any transplantable or implantable tissue, the survivability of which is improved by the methods described herein upon implantation. In particular, the overall durability and longevity of the implant are improved, and host-immune system mediated responses, are substantially eliminated.

The terms "transplant" and "implant" are used interchangeably to refer to tissue, material or cells (xenogeneic or allogeneic) which may be introduced into the body of a patient.

The terms "autologous" and "autograft" refer to tissue or cells which originate with or are derived from the recipient, whereas the terms "allogeneic" and "allograft" refer to cells and tissue which originate with or are derived from a donor of the same species as the recipient. The terms "xenogeneic" and "xenograft" refer to cells or tissue which originates with or are derived from a species other than that of the recipient.

The present invention is directed towards a cartilage repair construct constructed of two separate pieces of allograft cancellous bone.

Both pieces of the two-piece allograft construct are to be derived from dense cancellous bone that may originate from proximal or distal femur, proximal or distal tibia, proximal humerus, talus, calceneus, patella, or iliium. Cancellous tissue is first processed into blocks and then milled into the desired shapes. The top piece or cap member is substantially demineralized in dilute acid until the bone contains less than 0.2% wt/wt residual calcium. Subsequently, the resultant tissue form is predominantly Type I collagen, which is sponge-like in nature with an elastic quality. Following decalcification, the tissue is further cleaned and may also be treated so that the cancellous tissue is non-osteoinductive. This inactivation of inherent osteoinductivity may be accomplished via chemical or thermal treatment or by high energy irradiation. In a preferred embodiment, the cancellous cap member is treated with an oxidizing agent such as hydrogen peroxide in order to achieve a non-osteoinductive material. The bottom piece will be formed from mineralized cancellous bone or partially demineralized cancellous bone.

Figure 4:
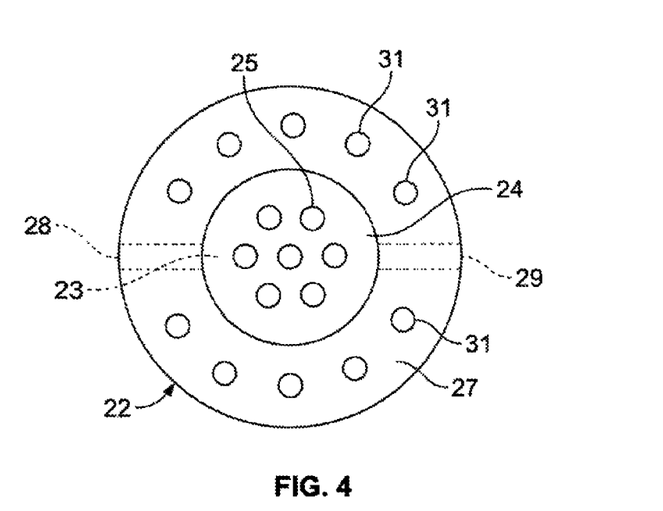
FIG. 4 is a top plan view of a base member employed by the construct of FIG. 3.
Figure 5:
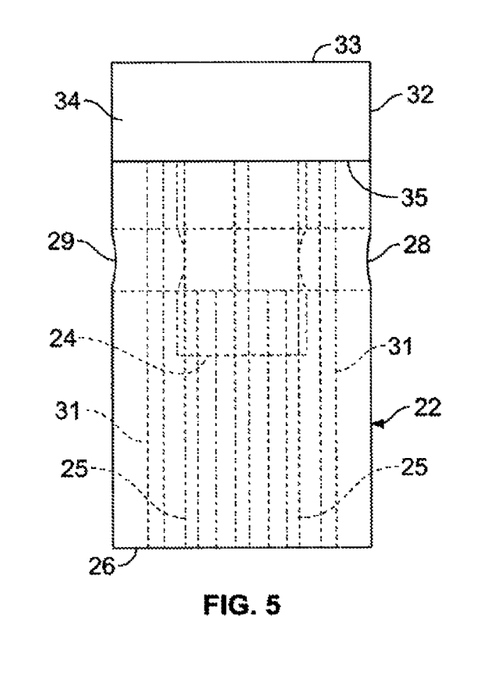
FIG. 5 is a side elevation view of a base member and a cap member employed by the construct of FIG. 3, wherein the cap member is mounted on the base member.
Figure 6:
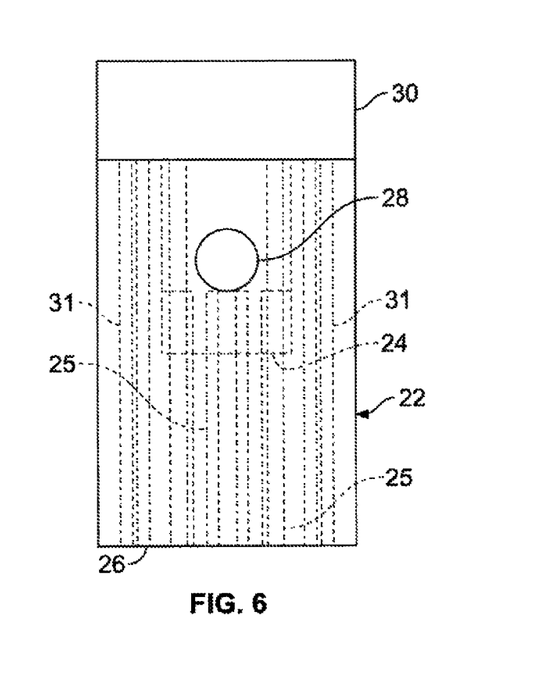
FIG. 6 is a side elevation view of the base member and cap member of the construct of FIG. 3, wherein the base member and cap member have been rotated 90° from their position shown in FIG. 5.
Figure 7:
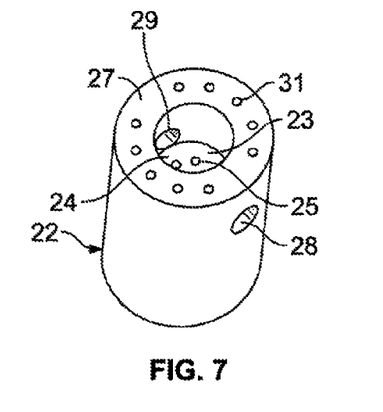
FIG. 7 is a top perspective view of the base member employed by the construct of FIG. 3.
Figure 8:
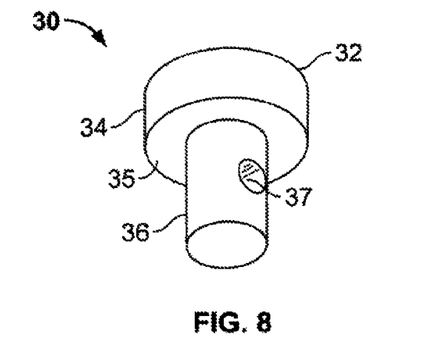
FIG. 8 is a bottom perspective view of the cap member employed by the construct of FIG. 3.
Figure 9:
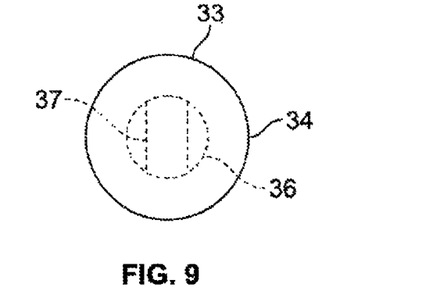
FIG. 9 is a top plan view of the cap member of FIG. 8.
Figure 10:
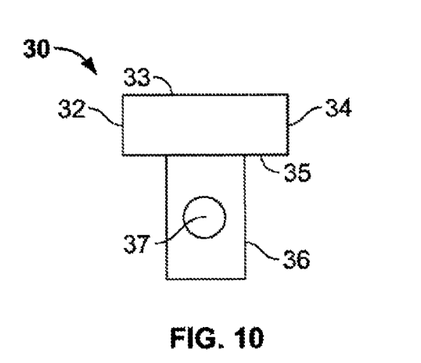
FIG. 10 is a side elevation view of the cap member of FIG. 8.
Figure 11:
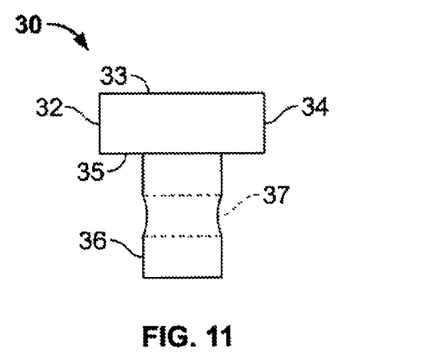
FIG. 11 is a side elevational view of the cap member of FIG. 8, wherein the cap member has been rotated 90° from its position shown in FIG. 10.

The two piece allograft cancellous construct 20 has a base member 22 with a cap member 30 which is held fixed in place in the base member 22 by a pin 40. The base member 22 is preferably constructed of mineralized cancellous bone and is shaped in the form of a cylinder for easy insertion into bores cut into the patient to cut away cartilage defect areas. However, the base member 22 may be surface or partially demineralized or contain a region of cortical bone so that it is cortical/cancellous. The body of the base member 22 defines a blind bore 23 which holds a stem 36 of the cap member 30, as further described below. The bottom surface 24 of the blind bore, as seen in FIGS. 5-7, has a plurality of longitudinal through-going bores 25 extending through the base member 22 and ending on the distal end surface 26 of the base member, which is preferably planar. The top surface 27 of the base member 22 is also preferably planar, forming a seat for the cap member 30. A first lateral bore 28 extends generally transversely from an exterior wall of the base member 22, above the bottom surface 24 of the blind bore 23, and intersects the blind bore 23. A second lateral bore 29 extends generally transversely from the exterior wall of the base member 22, above the bottom surface 24 of the blind bore 23, and intersects the blind bore 23 so as to be opposite the first lateral bore 28 (see FIGS. 4, 5 and 7) and in coaxial alignment therewith. A second plurality of longitudinal through-going bores 31 are circumferentially positioned around the blind bore 23 parallel to the central axis of the base member 22 and extend from the top surface 27 to the bottom surface 26. The longitudinal through-going bores 25 and 31 have a smaller diameter than the blind bore 23, with a diameter ranging from 0.5 to 2.0 mm.

The cap member 30 has a cylindrical top section 32 which has a thickness of about 3 mm with a top planar surface 33, an outer curved wall 34 and a bottom planar surface 35 which is seated adjacent the top surface 27 of the base member 22 when the components are mounted together. The top surface 33, while preferably planar may be milled to a degree of curvature that matches the physiological curvature. Larger constructs may have a cap member that has multiple stem sections and a base with an inverse "female" pattern which receives the stem sections.

The cap member 30 includes an integral cylindrical stem 36 that depends from the bottom planar surface 35 of the top section 32. The stem 36 has a length which is not longer than the depth of the blind bore 23 and has a diameter which is equal to or less than the diameter of the blind bore 23. The stem 36 includes a transverse radial bore 37 which is aligned with the first and second lateral bores 28, 29 of the base member 22 to receive a cylindrical pin 40. More particularly, the pin 40 is inserted radially through the construct 20 to hold the cap member 30 in place within the base member 22 (see FIG. 3). The cap member 30 is preferably formed of demineralized cancellous allograft bone with a calcium content of less than 0.2% calcium. Alternatively, the cap member 30 has a substantially demineralized region, such as the top section 32, with a calcium content of less than 0.2% calcium. The cylindrical pin 40 is preferably constructed of cortical bone and has a length equal to or less than the diameter of the base member 22. The pin 40 can also be constructed of a synthetic material.

The cap member 30 can be secured to the base member 22 by a staple, suture, press fit or an adhesive compound such as fibrin based glue.

The construct 20 is placed in a defect area bore which has been cut in the lesion area of the bone of a patient with the upper surface 26 of the cap member 30 being slightly proud, slightly below, or substantially flush with the surface of the original cartilage remaining at the area being treated. The construct 20 has a length which can be the same as the depth of the defect or more or less than the depth of the bore. If the construct 20 is the same as the depth of the bore 60, the base of the implant is supported by the bottom surface of the bore and the top surface 33 of cap 30 is substantially level with the articular cartilage. If the construct 20 is of a lesser length, the base of the construct is not supported but support is provided by the wall of the defect area bore or respective cut out area as the plug is interference fit within the bore or cut out area with the cap being slightly proud, slightly below, or flush with the surrounding articular cartilage depending on the surgeon's preference. With such load bearing support the graft surface is not damaged by weight or bearing loads which can cause micromotion interfering with the graft interface producing fibrous tissue interfaces and subchondral cysts.

Including the pluralities of longitudinal through-going bores 25 and 31 in the construct 20 facilitates cell migration throughout the construct 20. Such cell migration promotes cartilage growth in the cartilage area and bone growth in the adjacent bone region.

In operation, the lesion or defect is removed by cutting a bore removing a lesion in the implant area. If desired, the open cancellous structure of the cap member 30 may be loaded with a cartilage paste or gel as noted below and/or one or more additives namely recombinant or native growth factors (FGF-2, FGF-5, FGF-7, IGF-1, TGF-β, BMP-2, BMP-4, BMP-7, PDGF, VEGF), human allogenic or autologous chondrocytes, human allogenic cells, human allogenic or autologous bone marrow cells, human allogenic or autologous stem cells, demineralized bone matrix, insulin, insulin-like growth factor-1, interleukin-1 receptor antagonist, hepatocyte growth factor, platelet-derived growth factor, Indian hedgehog parathyroid hormone-related peptide, viral vectors for growth factor or DNA delivery, nanoparticles, or platelet-rich plasma. The construct 20 is then placed in the bore or cut away area in an interference fit with the surrounding walls.

If the construct is moveable within the bore, suitable organic glue material can be used to keep the implant fixed in place in the implant area. Suitable organic glue material can be found commercially, such as for example; USSEEL® or TISSUCOL® (fibrin based adhesive; Immuno AG, Austria), Adhesive Protein (Sigma Chemical, USA), Dow Corning Medical Adhesive B (Dow Corning, USA), fibrinogen thrombin, elastin, collagen, casein, albumin, keratin and the like.

The base of the blind bore 23 of the construct 20 can alternatively be provided with a matrix of minced cartilage putty or gel consisting of minced or milled allograft cartilage which has been lyophilized so that its water content ranges from 0.1% to 8.0% ranging from 25% to 50% by weight, mixed with a carrier of sodium hyaluronate solution (HA) (molecular weight ranging from $7.0 \times 10^5$ to $1.2 \times 10^6$) or any other bioabsorbable carrier such as hyaluronic acid and its derivatives, gelatin, collagen, chitosan, alginate, buffered PBS, Dextran, or polymers, the carrier ranging from ranging from 75% to 50% by weight. The cartilage is milled to a size ranging up to 1 mm.

In the gel form, the minced cartilage has been lyophilized so that its water content ranges from 0.1% to 8.0%, ranging from 15% to 30% by weight and the carrier ranges from 85% to 70% by weight. The particle size of the cartilage when milled is less than or equal to 1 mm dry. The cartilage pieces can be processed to varying particle sizes and the HA or other carrier can have different viscosities depending on the desired consistency of the putty or gel. This cartilage matrix can be deposited into the demineralized cap member. The putty or gel enhances the tissue integration between the plug and host tissue.

It is also envisioned that demineralized bone matrix and/or growth factors such as (FGF-2, FGF-5, FGF-7, IGF-1, TGF-β, BMP-2, BMP-4, BMP-7, PDGF, VEGF) or soluble factors such as insulin, interleukin-1 receptor antagonist, hepatocyte growth factor, Indian hedgehog and parathyroid hormone-related peptide, viral vectors for growth factor or DNA delivery, nanoparticles may be adsorbed or combined with the construct or the cartilage pieces. In another embodiment, platelet-rich plasma may be added to the construct.

It is also envisioned that cells which have been grown outside the patient can be inserted by syringe into the cancellous cap member 30 before, during or after deposit of the construct 20 into the defect area. Such cells include allogenic or autologous, bone marrow cells, stem cells and chondrocyte cells. The cellular density of the cells preferably ranges from $1.0 \times 10^8$ to $5.0 \times 10^8$ or from about 100 million to about 500 million cells per cc of putty or gel mixture. The cap member 30 can support the previously mentioned chondrogenic stimulating factors.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claim:

We claim:

1. In a multi-component construct for cartilage and bone repair, said construct having an outer periphery whose size and shape are selected such that said construct is positionable in a defect site to be repaired, said construct including a cap member shaped to form a stem having a longitudinal axis, which defines an axial direction, and a top section attached to one end of said stem and extending radially outward therefrom, said top section having first and second opposed surfaces, said first surface being sized and shaped so as to be adjacent an original cartilage layer at the defect site when said construct is positioned therein, and a base member sized and shaped so as to be adjacent a subchondral bone layer at the defect site when said construct is positioned therein, said base member including a proximal end proximate said second surface of said top section when said multi-component construct is assembled, a distal end remote from said cap member when said multi-component construct is assembled, and a blind bore extending in said axial direction from said proximal end toward said distal end, said blind bore being sized and shaped so as to receive said stem of said cap member, the improvement wherein:

said cap member is formed from a first piece of cancellous bone which is demineralized to thereby provide said top section and said stem of said cap member with an elastic quality, said top section including a first sidewall having a first diameter;

said base member is formed from a second, separate piece of cancellous bone that is mineralized, whereby said base member does not have an elastic quality, said base member including a second sidewall having a second diameter which is substantially equal to, but not greater than, said first diameter, whereby said proximal end of said base member is substantially coextensive with said top section of said cap member and wherein said first and second diameters are selected such that said outer periphery of said construct is delimited by said first sidewall of said top section of said cap member, and by said second sidewall of said base member; and said second surface of said top section of said cap member is in direct contact with said proximal end of said base member upon assembly of said multi-component construct, whereby said base member supports said top section such that said first surface of said top section is substantially flush with an outer surface of the original cartilage layer at the defect site.

2. The construct of claim 1, wherein said blind bore of said base member includes a bottom surface intermediate said proximal end of said base member and said distal end of said base member.

3. The construct of claim 2, wherein an opposite end of said stem, remote from said top section of said cap member, is in direct contact with said bottom surface of said blind bore of said base member upon assembly of said multi-component construct.

4. The construct of claim 1, wherein said first surface of said top section is a planar top surface.

5. The construct of claim 1, wherein said first piece of cancellous bone has a calcium content of less than 0.2%.

6. The construct of claim 1, wherein said cap member is treated to be non-osteoinductive.

* * * * *